(12) United States Patent
Mehigh et al.

(10) Patent No.: US 7,741,053 B2
(45) Date of Patent: Jun. 22, 2010

(54) PROCESSES FOR PURIFICATION OF RECOMBINANT PROTEINS

(75) Inventors: Richard J. Mehigh, St. Louis, MO (US); Eliezer Kopf, Rehovot (IL); Efrat Reem, Rehovot (IL); Edward B. Watson, III, Overland, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 809 days.

(21) Appl. No.: 11/128,486

(22) Filed: May 13, 2005

(65) Prior Publication Data

US 2006/0257927 A1 Nov. 16, 2006

(51) Int. Cl.
*C07K 1/22* (2006.01)
*C07K 16/44* (2006.01)
*G01N 33/53* (2006.01)

(52) U.S. Cl. ............... 435/7.1; 436/518; 530/387.9; 530/413

(58) Field of Classification Search .................. None
See application file for complete search history.

(56) References Cited

U.S. PATENT DOCUMENTS

| | | | |
|---|---|---|---|
| 4,569,794 A | 2/1986 | Smith et al. | |
| 4,703,004 A | 10/1987 | Hopp et al. | |
| 4,851,341 A | 7/1989 | Hopp et al. | |
| 5,011,912 A | 4/1991 | Hopp et al. | |
| 5,047,513 A | 9/1991 | Döbeli et al. | |
| 5,284,933 A | 2/1994 | Döbeli et al. | |
| 5,310,663 A | 5/1994 | Döbeli et al. | |
| 5,594,115 A | 1/1997 | Sharma | |
| 5,654,176 A | 8/1997 | Smith | |
| 5,750,374 A | 5/1998 | Dobeli et al. | |
| 5,932,102 A | 8/1999 | Wyllie et al. | |
| 6,193,966 B1 | 2/2001 | Deo et al. | |
| 6,462,254 B1 | 10/2002 | Vernachio et al. | |
| 7,094,548 B2 | 8/2006 | Brizzard et al. | |
| 2003/0045465 A1 | 3/2003 | Mixson | |
| 2003/0138839 A1* | 7/2003 | Li et al. | 435/7.1 |
| 2004/0029781 A1* | 2/2004 | Hernan et al. | 514/6 |

FOREIGN PATENT DOCUMENTS

WO    WO 01/81365 A2    11/2001

OTHER PUBLICATIONS

Watson et al, FASEB Journal, vol. 18, No. 8, suppl. S, p. C173, 2004.*
Brizzard, B.L., et al., "Immunoaffinity Purification of FLAG® Epitope-Tagged Bacterial Alkaline Phosphatase Using a Novel Monoclonal Antibody and Peptide Elution," BioTechniques, 1994, vol. 16(4), pp. 730-734.
Galfre, G., et al., "Chapter 1. Preparation of Monoclonal Antibodies," Methods in Enzymology, 1981, vol. 73, pp. 3-46, Academic Press, New York, New York.
Koren, E., et al., "Characterization of a Monoclonal Antibody that Binds Equally to All Apolipoprotein and Lipoprotein Forms of Human Plasma Apolipoprotein B. I. Specificity and Binding Studies," Biochim Biophys Acta, 1986, vol. 876, pp. 91-100.
Kunz, D., et al., "The Human Leukocyte Platelet-Activating Factor Receptor," J Biol Chem, 1992, vol. 267(13), pp. 9101-9106.
Lauritzen, C., et al., "BPTI and N-Terminal Extended Analogues Generated by Factor $X_a$ Cleavage and Cathepsin C Trimming of a Fusion Protein Expressed in *Escherichia coli*," Protein Expression and Purification, 1991, vol. 2, pp. 372-278.
Porath, J., et al., "Immobilized Metal Ion Affinity Adsorption and Immobilized Metal Ion Affinity Chromatography of Biomaterials. Serum Protein Affinities for Gel-Immobilized Iron and Nickel Ions," Biochemistry, 1983, vol. 22, pp. 1621-1630.
Rodriguez-Viciana, P., et al., "Role of Phosphoinositide 3-OH Kinase in Cell Transformation and Control of the Actin Cytoskeleton by Ras," Cell, 1997, vol. 89, pp. 457-467.
Smith, D.B., et al., "Single-step Purification of Polypeptides Expressed in *Escherichia coli* as Fusions with Glutathione S-Transferase," Gene, 1988, vol. 67(1), pp. 31-40.
Wu, J., et al., "Hexahistidine ($His_6$)-tag Dependent Protein Dimerization: A Cautionary Tale," Acta Biochimica Polonica, 1999, vol. 46(3), pp. 591-599.
"Chapter 7. Immunoprecipitation," Antibodies: A Laboratory Manual, 2nd Edition, 1988, pp. 223-255, Cold Spring Harbor Press, New York.
Watson, N., et al., "The MAT Tag System: A Novel Histidine-Based Metal Affinity Tag (MAT) System for Expression, Purification and Detection of Recombinant Fusion Proteins," 2004, Program No. 73.8, Sigma-Aldrich Co., 1 Page.
Watson, N., et al., "Expression, Purification and Detection of Recombinant Fusion Proteins Using the MAT Tag System," 2005, FASEB/ASBMB Experimental Biology, Poster No. 213.6, Sigma-Aldrich Co., 1 Page.
Borjigin et al., "Insertional mutagenesis as a probe of rhodopsin's topography, stability, and activity", Journal of Biological Chemistry, 1994, pp. 14715-14722, vol. 269, No. 2.
Campbell et al., "The Alternative Carboxyl Termini of Avian Cardiac and Brain Sarcoplasmic Reticulum/Endoplasmic Reticulum Ca2+-ATPases Are on Opposite Sides of the Membrane", Journal of Biological Chemistry, 1992, pp. 9321-9325, vol. 267, No. 13.
Chang, "Thrombin Specificity: Requirement for apolar amino acids adjacent to the thrombin cleavage site of polypeptide substrate", European Journal of Biochemistry, 1985, pp. 217-224, vol. 151.
Cubitt et al., "Understanding, improving and using green fluorescent proteins", Trends in Biochemical Science, 1995, pp. 448-455, vol. 20.
Dan et al., "Hamster UDP-N-Acetylglucosamine:Dolichol-P N-Acetylglucosamine-1-P Transferase Has Multiple Transmembrance Spans and a Critical Cytosolic Loop", Journal of Biological Chemistry, 1996, pp. 30717-30724, vol. 271, No. 48.

(Continued)

*Primary Examiner*—David A Saunders

(57) ABSTRACT

Processes for the detection and purification of peptides and proteins comprising a metal ion-affinity peptide having a high affinity for coordinated metals and also being highly antigenic are described. Antibodies for use in the processes are also described.

29 Claims, 2 Drawing Sheets

OTHER PUBLICATIONS

Dykes et al., "Expression of atrial natriuretic factor as a cleavable fusion protein with chloramphenicol acetyltransferase in Escherichia coli", European Journal of Biochemistry, 1988, pp. 411-416, vol. 174.

Germino et al., "Use of gene fusions and protein-protein interaction in the isolation of a biologically active regulatory protein: The replication initiator protein of plasmid R6K", Proceedings of the National Academy of Sciences USA, 1983, pp. 6848-6852, vol. 80.

Gorman et al., "Recombinant genomes which express chloramphenicol acetyltransferase in mammalian cells", Molecular and Cellular Biology, 1982, pp. 1044-1051, vol. 2, No. 9.

Maina at al., "An Escherichia coli vector to express and purify foreign proteins by fusion to and separation from maltose-binding protein", Gene, 1988, pp. 365-373, vol. 74.

Matsushima et al., "Purification and further characterization of enteropeptidase from porcine duodenum", Journal of Biochemistry, 1999, pp. 947-951, vol. 125.

Mordux et al., "Synthesis of Trisacryl Sorbents for Metal Chelate Chromatography: Application to Monokine Separation", Affinity Chromatography and Biological Recognition, 1983, pp. 275-278, Academic Press Inc.

Nagai at al., "Generation of beta-globin by sequence-specific proteolysis of a hybrid protein produced in Escherichia coli", Nature, 1984, pp. 810-812, vol. 309.

Nilsson et al., "Fusions to Staphylococcal Protein A", Methods in Enzymology, 1990, pp. 144-161, vol. 185.

Nygren at al., "Analysis and use of the serum albumin binding domains of streptococcal protein G", Journal of Molecular Recognition, 1988, pp. 69-74, vol. 1, No. 2.

Rumsfeld et al., "High-Throughput Assay for Inorganic Pyrophsphatases Using the Cytosolic Enzymes of Saccharomyces cerevisiae and Human as an Example", Protein Expression and Purification, 2000, pp, 303-309, vol. 18, No. 3.

Sano et al., "A streptavidin-metallothionein chimera that allows specific labeling of biological materials with many difference heavy metal ions", Proceedings of the National Academy of Sciences USA, 1992, pp. 1534-1538, vol. 89.

Sato et al., "Universal Template Plasmid for Introduction of the Triple-HA Epitope Sequence into Cloned Genes", Biotechniques, 1997, pp. 254-256, vol. 23, No. 2.

Shoseyov et al., "Primary sequence analysis of Clostridium cellulovorans cellulose binding protein A", Proceedings of the National Academy of Sciences, 1992, pp. 3483-3487, vol. 89, No. 8.

Small et al., " High Performance Metal Chelate Chromatography", Affinity Chromatography and Biological Recognition, 1983, pp. 267-268, Academic Press Inc.

Vijayalakshmi, "High Performance Liquid Chromatography with Immobilised Metal Adsorbents", Affinity Chromatography and Biological Recognition, 1983, pp. 269-273, Academic Press.

Zheng et al., "A new expression vector for high level protein production, one step purification and direct isotopic labeling of calmodulin-binding peptide fusion proteins", Gene, 1997, pp. 55-60, vol. 186.

Non-Final Office Action dated Sep. 24, 2009, issued in U.S. Appl. No. 10/960,524, 11 pages.

Final Office Action dated Apr. 16, 2009, issued in U.S. Appl. No. 10/460,524, 8 pages.

Non-Final Office Action dated Apr. 18, 2008, issued in U.S. Appl. No. 10/460,524, 10 pages.

Non-Final Office Action dated Jan. 30, 2007, issued in U.S. Appl. No. 10/460,524, 6 pages.

Non-Final Office Action dated Aug. 1, 2006, issued in U.S. Appl. No. 10/460,524, 6 pages.

* cited by examiner

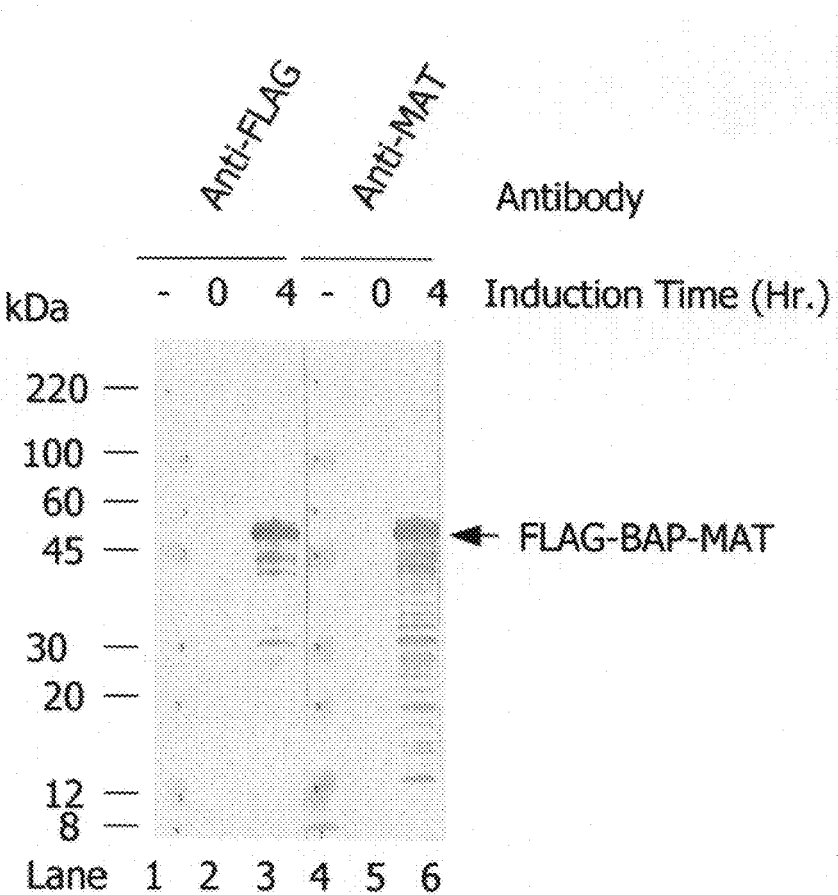

SEQUENCE LISTING

<160> NUMBER OF SEQ ID NOS: 42

<210> SEQ ID NO 1
<211> LENGTH: 211
<212> TYPE: PRT
<213> ORGANISM: Shistosoma japonicum

<400> SEQUENCE: 1

```
Met Ala Cys Gly His Val Lys Leu Ile Tyr Phe Asn Gly Arg Gly Arg
1               5                   10                  15

Ala Glu Pro Ile Arg Met Ile Leu Val Ala Ala Gly Val Glu Phe Glu
            20                  25                  30

Asp Glu Arg Ile Glu Phe Gln Asp Trp Pro Lys Ile Lys Pro Thr Ile
        35                  40                  45

Pro Gly Gly Arg Leu Pro Ile Val Lys Ile Thr Asp Lys Arg Gly Asp
    50                  55                  60

Val Lys Thr Met Ser Glu Ser Leu Ala Ile Ala Arg Phe Ile Ala Arg
65                  70                  75                  80

Lys His Asn Met Met Gly Asp Thr Asp Asp Glu Tyr Tyr Ile Ile Glu
                85                  90                  95

Lys Met Ile Gly Gln Val Glu Asp Val Glu Ser Asp Tyr His Lys Thr
            100                 105                 110

Leu Ile Lys Pro Pro Glu Glu Lys Glu Lys Ile Ser Lys Glu Ile Leu
        115                 120                 125

Asn Gly Lys Val Pro Ile Leu Leu Gln Ala Ile Cys Glu Thr Leu Lys
    130                 135                 140

Glu Ser Thr Gly Asn Leu Thr Val Gly Asp Lys Val Thr Leu Ala Asp
145                 150                 155                 160

Val Val Leu Ile Ala Ser Ile Asp His Ile Thr Asp Leu Asp Lys Glu
                165                 170                 175

Phe Leu Thr Gly Lys Tyr Pro Glu Ile His Lys His Arg Lys His Leu
            180                 185                 190

Leu Ala Thr Ser Pro Lys Leu Ala Lys Tyr Leu Ser Glu Arg His Ala
        195                 200                 205

Thr Ala Phe
    210
```

<210> SEQ ID NO 2
<211> LENGTH: 163
<212> TYPE: PRT
<213> ORGANISM: Clostridium cellulovorans

<400> SEQUENCE: 2

```
Ala Ala Thr Ser Ser Met Ser Val Glu Phe Tyr Asn Ser Asn Lys Ser
1               5                   10                  15

Ala Gln Thr Asn Ser Ile Thr Pro Ile Ile Lys Ile Thr Asn Thr Ser
            20                  25                  30

Asp Ser Asp Leu Asn Leu Asn Asp Val Lys Val Arg Tyr Thr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65                  70                  75                  80

Asn Phe Val Lys Glu Thr Ala Ser Pro Thr Ser Thr Tyr Asp Thr Tyr
                85                  90                  95
```

Val Glu Phe Gly Phe Ala Ser Gly Ala Ala Thr Leu Lys Lys Gly Gln
            100                 105                 110

Phe Ile Thr Ile Gln Gly Arg Ile Thr Lys Ser Asp Trp Ser Asn Tyr
            115                 120                 125

Thr Gln Thr Asn Asp Tyr Ser Phe Asp Ala Ser Ser Ser Thr Pro Val
130                 135                 140

Val Asn Pro Lys Val Thr Gly Tyr Ile Gly Gly Ala Lys Val Leu Gly
145                 150                 155                 160

Thr Ala Pro

<210> SEQ ID NO 3
<211> LENGTH: 396
<212> TYPE: PRT
<213> ORGANISM: Escherichia coli

<400> SEQUENCE: 3

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

```
Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
                355                 360                 365

Val Arg Thr Ala Val Ile Asn Ala Ala Ser Gly Arg Gln Thr Val Asp
            370                 375                 380

Glu Ala Leu Lys Asp Ala Gln Thr Arg Ile Thr Lys
385                 390                 395

<210> SEQ ID NO 4
<211> LENGTH: 524
<212> TYPE: PRT
<213> ORGANISM: Staphylococcus aureus

<400> SEQUENCE: 4

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
                20                  25                  30

Ala Ala Asn Ala Ala Gln His Asp Glu Ala Gln Gln Asn Ala Phe Tyr
            35                  40                  45

Gln Val Leu Asn Met Pro Asn Leu Asn Ala Asp Gln Arg Asn Gly Phe
        50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
```

-continued

```
                275                 280                 285
Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
            355                 360                 365

Glu Asp Asn Asn Lys Pro Gly Lys Glu Asp Gly Asn Lys Pro Gly Lys
            370                 375                 380

Glu Asp Asn Lys Lys Pro Gly Lys Glu Asp Gly Asn Lys Pro Gly Lys
385                 390                 395                 400

Glu Asp Asn Lys Lys Pro Gly Lys Glu Asp Gly Asn Lys Pro Gly Lys
                405                 410                 415

Glu Asp Gly Asn Lys Pro Gly Lys Glu Asp Gly Asn Gly Val His Val
            420                 425                 430

Val Lys Pro Gly Asp Thr Val Asn Asp Ile Ala Lys Ala Asn Gly Thr
        435                 440                 445

Thr Ala Asp Lys Ile Ala Ala Asp Asn Lys Leu Ala Asp Lys Asn Met
            450                 455                 460

Ile Lys Pro Gly Gln Glu Leu Val Val Asp Lys Lys Gln Pro Ala Asn
465                 470                 475                 480

His Ala Asp Ala Asn Lys Ala Gln Ala Leu Pro Glu Thr Gly Glu Glu
                485                 490                 495

Asn Pro Phe Ile Gly Thr Thr Val Phe Gly Gly Leu Ser Leu Ala Leu
            500                 505                 510

Gly Ala Ala Leu Leu Ala Gly Arg Arg Arg Glu Leu
            515                 520

<210> SEQ ID NO 5
<211> LENGTH: 448
<212> TYPE: PRT
<213> ORGANISM: Streptococcus

<400> SEQUENCE: 5

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Asp Ala Leu Ala Lys Ala Lys Ala Asp Ala Leu
            100                 105                 110

Lys Glu Phe Asn Lys Tyr Gly Val Ser Asp Tyr Tyr Lys Asn Leu Ile
            115                 120                 125
```

```
Asn Asn Ala Lys Thr Val Glu Gly Ile Lys Asp Leu Gln Ala Gln Val
    130                 135                 140
Val Glu Ser Ala Lys Lys Ala Arg Ile Ser Glu Ala Thr Asp Gly Leu
145                 150                 155                 160
Ser Asp Phe Leu Lys Ser Gln Thr Pro Ala Glu Asp Thr Val Lys Ser
                165                 170                 175
Ile Glu Leu Ala Glu Ala Lys Val Leu Ala Asn Arg Glu Leu Asp Lys
            180                 185                 190
Tyr Gly Val Ser Asp Tyr His Lys Asn Leu Ile Asn Asn Ala Lys Thr
        195                 200                 205
Val Glu Gly Val Lys Glu Leu Ile Asp Glu Ile Leu Ala Ala Leu Pro
    210                 215                 220
Lys Thr Asp Thr Tyr Lys Leu Ile Leu Asn Gly Lys Thr Leu Lys Gly
225                 230                 235                 240
Glu Thr Thr Thr Glu Ala Val Asp Ala Ala Thr Ala Glu Lys Val Phe
                245                 250                 255
Lys Gln Tyr Ala Asn Asp Asn Gly Val Asp Gly Glu Trp Thr Tyr Asp
            260                 265                 270
Asp Ala Thr Lys Thr Phe Thr Val Thr Glu Lys Pro Glu Val Ile Asp
        275                 280                 285
Ala Ser Glu Leu Thr Pro Ala Val Thr Thr Tyr Lys Leu Val Ile Asn
    290                 295                 300
Gly Lys Thr Leu Lys Gly Glu Thr Thr Thr Lys Ala Val Asp Ala Glu
305                 310                 315                 320
Thr Ala Glu Lys Ala Phe Lys Gln Tyr Ala Asn Asp Asn Gly Val Asp
                325                 330                 335
Gly Val Trp Thr Tyr Asp Asp Ala Thr Lys Thr Phe Thr Val Thr Glu
            340                 345                 350
Met Val Thr Glu Val Pro Gly Asp Ala Pro Thr Glu Pro Glu Lys Pro
        355                 360                 365
Glu Ala Ser Ile Pro Leu Val Pro Leu Thr Pro Ala Thr Pro Ile Ala
    370                 375                 380
Lys Asp Asp Ala Lys Lys Asp Asp Thr Lys Lys Glu Asp Ala Lys Lys
385                 390                 395                 400
Pro Glu Ala Lys Lys Asp Asp Ala Lys Lys Ala Glu Thr Leu Pro Thr
                405                 410                 415
Thr Gly Glu Gly Ser Asn Pro Phe Phe Thr Ala Ala Ala Leu Ala Val
            420                 425                 430
Met Ala Gly Ala Gly Ala Leu Ala Val Ala Ser Lys Arg Lys Glu Asp
        435                 440                 445

<210> SEQ ID NO 6
<211> LENGTH: 192
<212> TYPE: PRT
<213> ORGANISM: Homo sapiens

<400> SEQUENCE: 6

Met Ala Pro Ser Leu Ser Ala Met Thr Pro Trp Thr Pro Gly Pro Ser
1               5                   10                  15
Trp Ser Ser Val Tyr Met Thr Cys Val Trp Ser Val Gly Ser Gly Ser
            20                  25                  30
Ala Cys Ala Val Ala Ser Ala Pro Met Pro Arg Pro Val Trp Ser Leu
        35                  40                  45
Ala Ser Arg Leu Gly Thr Gly Asp His Gln Pro Thr Ala Pro Cys Pro
    50                  55                  60
```

```
Ala Leu Pro Thr Ala Ala Met Ser Ser Ala Ala Leu Leu Ala Arg Pro
 65                  70                  75                  80

Pro Ala Thr Gly Leu Arg Arg Arg Pro Thr Ala Pro Gly Ala Pro Ala
                 85                  90                  95

Trp Arg Ala Ala Cys Ala Ser Gln Ala Ser Trp Pro Ala Ala Ala Pro
                100                 105                 110

Ala Cys Arg Pro Arg Arg Val Ala Ala Pro Ser Arg Val Ser Ser Ser
            115                 120                 125

Leu Arg Ala Arg Lys Cys Gly Arg Thr Ser Cys Ala Lys Gly Ala Ala
        130                 135                 140

Pro Ala Thr Ala Pro Pro Ile Arg Ser Pro Ala Ala Thr Ser Arg Ala
145                 150                 155                 160

Ala Arg Arg Val Ser Ala Ala Ser Arg Thr Ala Ser Trp Ala Ala
                165                 170                 175

Thr Pro Ile Ala Ser Gly Pro Ala Arg Gly Pro Gly Thr His Thr Met
                180                 185                 190

<210> SEQ ID NO 7
<211> LENGTH: 216
<212> TYPE: PRT
<213> ORGANISM: Escherichia coli

<400> SEQUENCE: 7

Met Asn Phe Asn Lys Ile Asp Leu Asp Asn Trp Lys Arg Lys Glu Ile
  1               5                  10                  15

Phe Asn His Tyr Leu Asn Gln Gln Thr Thr Phe Ser Ile Thr Thr Glu
                 20                  25                  30

Ile Asp Ile Ser Val Leu Tyr Arg Asn Ile Lys Gln Glu Gly Tyr Lys
             35                  40                  45

Phe Tyr Pro Ala Phe Ile Phe Leu Val Thr Arg Val Ile Asn Ser Asn
     50                  55                  60

Thr Ala Phe Arg Thr Gly Tyr Asn Ser Asp Gly Glu Leu Gly Tyr Trp
 65                  70                  75                  80

Asp Lys Leu Glu Pro Leu Tyr Thr Ile Phe Asp Gly Val Ser Lys Thr
                 85                  90                  95

Phe Ser Gly Ile Trp Thr Pro Val Lys Asn Asp Phe Lys Glu Phe Tyr
                100                 105                 110

Asp Leu Tyr Leu Ser Asp Val Glu Lys Tyr Asn Gly Ser Gly Lys Leu
            115                 120                 125

Phe Pro Lys Thr Pro Ile Pro Glu Asn Ala Phe Ser Leu Ser Ile Ile
        130                 135                 140

Pro Trp Thr Ser Phe Thr Gly Phe Asn Leu Asn Ile Asn Asn Asn Ser
145                 150                 155                 160

Asn Tyr Leu Leu Pro Ile Ile Thr Ala Gly Lys Phe Ile Asn Lys Gly
                165                 170                 175

Asn Ser Ile Tyr Leu Pro Leu Ser Leu Gln Val His Ser Val Cys
                180                 185                 190

Asp Gly Tyr His Ala Gly Leu Phe Met Asn Ser Ile Gln Glu Leu Ser
            195                 200                 205

Asp Arg Pro Asn Asp Trp Leu Leu
        210                 215

<210> SEQ ID NO 8
<211> LENGTH: 160
<212> TYPE: PRT
```

<213> ORGANISM: Streptomyces avidinii

<400> SEQUENCE: 8

```
Met Asp Pro Ser Lys Asp Ser Lys Ala Gln Val Ser Ala Ala Glu Ala
1               5                   10                  15

Gly Ile Thr Gly Thr Trp Tyr Asn Gln Leu Gly Ser Thr Phe Ile Val
            20                  25                  30

Thr Ala Gly Ala Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Thr Asp Gly Ser Gly Thr Ala Leu Gly Trp Thr Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Ala Asn Ala Trp Lys Ser Thr Leu Val Gly His
        115                 120                 125

Asp Thr Phe Thr Lys Val Lys Pro Ser Ala Ala Ser Ile Asp Ala Ala
    130                 135                 140

Lys Lys Ala Gly Val Asn Asn Gly Asn Pro Leu Asp Ala Val Gln Gln
145                 150                 155                 160
```

<210> SEQ ID NO 9
<211> LENGTH: 1024
<212> TYPE: PRT
<213> ORGANISM: Escherichia coli

<400> SEQUENCE: 9

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
```

-continued

```
            195                 200                 205
Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
    290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
    370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
        435                 440                 445

Arg Asn His Pro Ser Val Ile Ile Trp Ser Leu Gly Asn Glu Ser Gly
    450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
        515                 520                 525

Gly Glu Thr Arg Pro Leu Ile Leu Cys Glu Tyr Ala His Ala Met Gly
    530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
                565                 570                 575

Ile Lys Tyr Asp Glu Asn Gly Asn Pro Trp Ser Ala Tyr Gly Gly Asp
            580                 585                 590

Phe Gly Asp Thr Pro Asn Asp Arg Gln Phe Cys Met Asn Gly Leu Val
        595                 600                 605

Phe Ala Asp Arg Thr Pro His Pro Ala Leu Thr Glu Ala Lys His Gln
    610                 615                 620
```

-continued

```
Gln Gln Phe Phe Gln Phe Arg Leu Ser Gly Gln Thr Ile Glu Val Thr
625                 630                 635                 640

Ser Glu Tyr Leu Phe Arg His Ser Asp Asn Glu Leu Leu His Trp Met
            645                 650                 655

Val Ala Leu Asp Gly Lys Pro Leu Ala Ser Gly Glu Val Pro Leu Asp
        660                 665                 670

Val Ala Pro Gln Gly Lys Gln Leu Ile Glu Leu Pro Glu Leu Pro Gln
    675                 680                 685

Pro Glu Ser Ala Gly Gln Leu Trp Leu Thr Val Arg Val Gln Pro
690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
            725                 730                 735

Ala Ile Pro His Leu Thr Thr Ser Glu Met Asp Phe Cys Ile Glu Leu
        740                 745                 750

Gly Asn Lys Arg Trp Gln Phe Asn Arg Gln Ser Gly Phe Leu Ser Gln
    755                 760                 765

Met Trp Ile Gly Asp Lys Lys Gln Leu Leu Thr Pro Leu Arg Asp Gln
770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
            805                 810                 815

Tyr Gln Ala Glu Ala Ala Leu Leu Gln Cys Thr Ala Asp Thr Leu Ala
        820                 825                 830

Asp Ala Val Leu Ile Thr Thr Ala His Ala Trp Gln His Gln Gly Lys
    835                 840                 845

Thr Leu Phe Ile Ser Arg Lys Thr Tyr Arg Ile Asp Gly Ser Gly Gln
850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
            885                 890                 895

Asn Trp Leu Gly Leu Gly Pro Gln Glu Asn Tyr Pro Asp Arg Leu Thr
        900                 905                 910

Ala Ala Cys Phe Asp Arg Trp Asp Leu Pro Leu Ser Asp Met Tyr Thr
    915                 920                 925

Pro Tyr Val Phe Pro Ser Glu Asn Gly Leu Arg Cys Gly Thr Arg Glu
930                 935                 940

Leu Asn Tyr Gly Pro His Gln Trp Arg Gly Asp Phe Gln Phe Asn Ile
945                 950                 955                 960

Ser Arg Tyr Ser Gln Gln Gln Leu Met Glu Thr Ser His Arg His Leu
            965                 970                 975

Leu His Ala Glu Glu Gly Thr Trp Leu Asn Ile Asp Gly Phe His Met
        980                 985                 990

Gly Ile Gly Gly Asp Asp Ser Trp Ser Pro Ser Val Ser Ala Glu Phe
    995                 1000                1005

Gln Leu Ser Ala Gly Arg Tyr His Tyr Gln Leu Val Trp Cys Gln
    1010                1015                1020

Lys
```

<210> SEQ ID NO 10
<211> LENGTH: 238
<212> TYPE: PRT
<213> ORGANISM: Aequorea victoria

<400> SEQUENCE: 10

Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Gly Ile Thr His Gly Met Asp Glu Leu Tyr Lys
225                 230                 235

<210> SEQ ID NO 11
<211> LENGTH: 109
<212> TYPE: PRT
<213> ORGANISM: Escherichia coli

<400> SEQUENCE: 11

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala

<210> SEQ ID NO 12
<211> LENGTH: 13
<212> TYPE: PRT
<213> ORGANISM: Oryctolagus cuniculus

<400> SEQUENCE: 12

Ile Ala Val Ser Ala Ala Asn Arg Phe Lys Lys Ile Ser
1               5                   10

<210> SEQ ID NO 13
<211> LENGTH: 10
<212> TYPE: PRT
<213> ORGANISM: artificial sequence
<220> FEATURE:
<223> OTHER INFORMATION: synthetic c-myc epitope

<400> SEQUENCE: 13

Glu Gln Lys Leu Ile Ser Glu Glu Asp Leu
1               5                   10

<210> SEQ ID NO 14
<211> LENGTH: 7
<212> TYPE: PRT
<213> ORGANISM: artificial sequence
<220> FEATURE:
<223> OTHER INFORMATION: synthetic HA epitope

<400> SEQUENCE: 14

Tyr Pro Tyr Asp Val Tyr Ala
1               5

<210> SEQ ID NO 15
<211> LENGTH: 8
<212> TYPE: PRT
<213> ORGANISM: artificial sequence
<220> FEATURE:
<223> OTHER INFORMATION: synthetic FLAG sequence

<400> SEQUENCE: 15

Asp Tyr Lys Asp Asp Asp Asp Lys
1               5

<210> SEQ ID NO 16
<211> LENGTH: 8
<212> TYPE: PRT
<213> ORGANISM: artificial sequence
<220> FEATURE:
<223> OTHER INFORMATION: synthetic Invitorgen sequence

<400> SEQUENCE: 16

Asp Leu Tyr Asp Asp Asp Asp Lys
1               5

<210> SEQ ID NO 17
<211> LENGTH: 23
<212> TYPE: PRT
<213> ORGANISM: artificial sequence
<220> FEATURE:
<223> OTHER INFORMATION: synthetic 3X FLAG sequence

<400> SEQUENCE: 17

Met Asp Tyr Lys Asp His Asp Gly Asp Tyr Lys Asp His Asp Ile Asp
1               5                   10                  15

Tyr Lys Asp Asp Asp Asp Lys

<210> SEQ ID NO 18
<211> LENGTH: 30
<212> TYPE: DNA
<213> ORGANISM: artificial sequence
<220> FEATURE:
<223> OTHER INFORMATION: chemically synthesized oligonucleotide
<220> FEATURE:
<221> NAME/KEY: misc_feature
<222> LOCATION: (10)..(10)
<223> OTHER INFORMATION: N= A, G, T or C
<220> FEATURE:
<221> NAME/KEY: misc_feature
<222> LOCATION: (9)..(9)
<223> OTHER INFORMATION: D=A, G, or T
<220> FEATURE:
<221> NAME/KEY: misc_feature
<222> LOCATION: (11)..(11)
<223> OTHER INFORMATION: D=A, G, or T
<220> FEATURE:
<221> NAME/KEY: misc_feature
<222> LOCATION: (15)..(15)
<223> OTHER INFORMATION: D=A, G, or T
<220> FEATURE:
<221> NAME/KEY: misc_feature
<222> LOCATION: (17)..(17)
<223> OTHER INFORMATION: D=A, G, or T
<220> FEATURE:
<221> NAME/KEY: misc_feature
<222> LOCATION: (21)..(21)
<223> OTHER INFORMATION: D=A, G, or T
<220> FEATURE:
<221> NAME/KEY: misc_feature
<222> LOCATION: (23)..(23)
<223> OTHER INFORMATION: D=A, G, or T
<220> FEATURE:
<221> NAME/KEY: misc_feature
<222> LOCATION: (16)..(16)
<223> OTHER INFORMATION: N= A, G, T or C
<220> FEATURE:
<221> NAME/KEY: misc_feature
<222> LOCATION: (22)..(22)
<223> OTHER INFORMATION: N= A, G, T or C

<400> SEQUENCE: 18
gatcccatdn dcatdndcat dndcattaac                               30

<210> SEQ ID NO 19
<211> LENGTH: 30
<212> TYPE: DNA
<213> ORGANISM: artificial sequence
<220> FEATURE:
<223> OTHER INFORMATION: chemically synthesized oligonucleotide
<220> FEATURE:
<221> NAME/KEY: misc_feature
<222> LOCATION: (13)..(13)
<223> OTHER INFORMATION: N= A, G, T, or C
<220> FEATURE:
<221> NAME/KEY: misc_feature
<222> LOCATION: (14)..(14)
<223> OTHER INFORMATION: H= A, C, or T
<220> FEATURE:
<221> NAME/KEY: misc_feature
<222> LOCATION: (18)..(18)
<223> OTHER INFORMATION: H= A, C, or T
<220> FEATURE:
<221> NAME/KEY: misc_feature
<222> LOCATION: (20)..(20)
<223> OTHER INFORMATION: H= A, C, or T
<220> FEATURE:
<221> NAME/KEY: misc_feature
<222> LOCATION: (24)..(24)
<223> OTHER INFORMATION: H= A, C, or T
<220> FEATURE:
<221> NAME/KEY: misc_feature

```
<222> LOCATION: (26)..(26)
<223> OTHER INFORMATION: H= A, C, or T
<220> FEATURE:
<221> NAME/KEY: misc_feature
<222> LOCATION: (19)..(19)
<223> OTHER INFORMATION: N= A, G, T, or C
<220> FEATURE:
<221> NAME/KEY: misc_feature
<222> LOCATION: (25)..(25)
<223> OTHER INFORMATION: N= A, G, T, or C
<220> FEATURE:
<221> NAME/KEY: misc_feature
<222> LOCATION: (12)..(12)
<223> OTHER INFORMATION: H= A, C, or T

<400> SEQUENCE: 19
aattgttaat ghnhatghnh atghnhatgg                                    30

<210> SEQ ID NO 20
<211> LENGTH: 26
<212> TYPE: DNA
<213> ORGANISM: artificial sequence
<220> FEATURE:
<223> OTHER INFORMATION: chemically synthesized oligonucleotide

<400> SEQUENCE: 20
tatgcataat catcgacatg aacata                                        26

<210> SEQ ID NO 21
<211> LENGTH: 28
<212> TYPE: DNA
<213> ORGANISM: artificial sequence
<220> FEATURE:
<223> OTHER INFORMATION: chemically synthesized oligonucleotide

<400> SEQUENCE: 21
agcttatgtt tatgtcgatg attatgca                                      28

<210> SEQ ID NO 22
<211> LENGTH: 26
<212> TYPE: DNA
<213> ORGANISM: artificial sequence
<220> FEATURE:
<223> OTHER INFORMATION: chemically synthesized oligonucleotide

<400> SEQUENCE: 22
tatgcataaa catagacatg ggcata                                        26

<210> SEQ ID NO 23
<211> LENGTH: 29
<212> TYPE: DNA
<213> ORGANISM: artificial sequence
<220> FEATURE:
<223> OTHER INFORMATION: chemically synthesized oligonucleotide

<400> SEQUENCE: 23
agcttgatgc ccatgtctat gtttatgca                                     29

<210> SEQ ID NO 24
<211> LENGTH: 7
<212> TYPE: PRT
<213> ORGANISM: Artificial Sequence
<220> FEATURE:
<223> OTHER INFORMATION: metal-ion affinity peptide
<220> FEATURE:
<221> NAME/KEY: MISC_FEATURE
<222> LOCATION: (2)..(2)
<223> OTHER INFORMATION: Xaa = any amino acid selected from the
      following group: Ala or Arg or Asn or Asp or Gln or Glu or Ile or
```

```
        Lys or Phe or Pro of Ser or Thr or Trp or Val.
<220> FEATURE:
<221> NAME/KEY: MISC_FEATURE
<222> LOCATION: (6)..(6)
<223> OTHER INFORMATION: Xaa = any amino acid selected from the
      following group: Ala or Arg or Asn or Asp or Cys or Gln or Glu or
      Gly or Ile or Leu or Lys or Met or Pro or Ser or Thr or Tyr or
      Val.

<400> SEQUENCE: 24

His Xaa His Arg His Xaa His
1               5

<210> SEQ ID NO 25
<211> LENGTH: 4
<212> TYPE: PRT
<213> ORGANISM: Artificial Sequence
<220> FEATURE:
<223> OTHER INFORMATION: enterokinase substrate sequence

<400> SEQUENCE: 25

Asp Asp Asp Lys
1

<210> SEQ ID NO 26
<211> LENGTH: 5
<212> TYPE: PRT
<213> ORGANISM: Artificial Sequence
<220> FEATURE:
<223> OTHER INFORMATION: enterokinase substrate sequence

<400> SEQUENCE: 26

Asp Asp Asp Asp Lys
1               5

<210> SEQ ID NO 27
<211> LENGTH: 6
<212> TYPE: PRT
<213> ORGANISM: Artificial Sequence
<220> FEATURE:
<223> OTHER INFORMATION: thrombin cleavage site sequence
<220> FEATURE:
<221> NAME/KEY: MISC_FEATURE
<222> LOCATION: (6)..(6)
<223> OTHER INFORMATION: Xaa = any non-acidic amino acid

<400> SEQUENCE: 27

Leu Val Pro Arg Gly Xaa
1               5

<210> SEQ ID NO 28
<211> LENGTH: 5
<212> TYPE: PRT
<213> ORGANISM: Artificial Sequence
<220> FEATURE:
<223> OTHER INFORMATION: Factor Xa protease cleavage site sequence
<220> FEATURE:
<221> NAME/KEY: MISC_FEATURE
<222> LOCATION: (5)..(5)
<223> OTHER INFORMATION: Xaa = any amino acid except proline or arginine

<400> SEQUENCE: 28

Ile Glu Gly Arg Xaa
1               5

<210> SEQ ID NO 29
<211> LENGTH: 5
<212> TYPE: PRT
<213> ORGANISM: Artificial Sequence
```

```
<220> FEATURE:
<223> OTHER INFORMATION: Factor Xa protease cleavage site sequence
<220> FEATURE:
<221> NAME/KEY: MISC_FEATURE
<222> LOCATION: (5)..(5)
<223> OTHER INFORMATION: Xaa = any amino acid except proline or arginine

<400> SEQUENCE: 29

Ile Asp Gly Arg Xaa
1               5

<210> SEQ ID NO 30
<211> LENGTH: 5
<212> TYPE: PRT
<213> ORGANISM: Artificial Sequence
<220> FEATURE:
<223> OTHER INFORMATION: Factor Xa protease cleavage site sequence
<220> FEATURE:
<221> NAME/KEY: MISC_FEATURE
<222> LOCATION: (5)..(5)
<223> OTHER INFORMATION: Xaa = any amino acid except proline or arginine

<400> SEQUENCE: 30

Ala Glu Gly Arg Xaa
1               5

<210> SEQ ID NO 31
<211> LENGTH: 6
<212> TYPE: PRT
<213> ORGANISM: Artificial Sequence
<220> FEATURE:
<223> OTHER INFORMATION: antigenic domain sequence
<220> FEATURE:
<221> NAME/KEY: MISC_FEATURE
<222> LOCATION: (4)..(5)
<223> OTHER INFORMATION: Xaa = independent amino acid residues

<400> SEQUENCE: 31

Asp Tyr Lys Xaa Xaa Asp
1               5

<210> SEQ ID NO 32
<211> LENGTH: 8
<212> TYPE: PRT
<213> ORGANISM: Artificial Sequence
<220> FEATURE:
<223> OTHER INFORMATION: linking sequence with enterokinase linkable
      site
<220> FEATURE:
<221> NAME/KEY: MISC_FEATURE
<222> LOCATION: (4)..(5)
<223> OTHER INFORMATION: Xaa = independent amino acid residues
<220> FEATURE:
<221> NAME/KEY: MISC_FEATURE
<222> LOCATION: (7)..(7)
<223> OTHER INFORMATION: Xaa = independent amino acid residue

<400> SEQUENCE: 32

Asp Tyr Lys Xaa Xaa Asp Xaa Lys
1               5

<210> SEQ ID NO 33
<211> LENGTH: 5
<212> TYPE: PRT
<213> ORGANISM: Artificial Sequence
<220> FEATURE:
<223> OTHER INFORMATION: antigenic domain sequence
<220> FEATURE:
<221> NAME/KEY: MISC_FEATURE
<222> LOCATION: (2)..(2)
<223> OTHER INFORMATION: Xaa = any amino acid
```

```
<220> FEATURE:
<221> NAME/KEY: MISC_FEATURE
<222> LOCATION: (4)..(5)
<223> OTHER INFORMATION: Xaa = any amino acid

<400> SEQUENCE: 33

Asp Xaa Tyr Xaa Xaa
1               5

<210> SEQ ID NO 34
<211> LENGTH: 8
<212> TYPE: PRT
<213> ORGANISM: Artificial Sequence
<220> FEATURE:
<223> OTHER INFORMATION: linking sequence with enterokinase linkable
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = any amino acid

<400> SEQUENCE: 34

Asp Xaa Tyr Xaa Xaa Asp Xaa Lys
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic MAT tag sequence

<400> SEQUENCE: 35

His Asn His Arg His Lys His Gly Gly Gly Cys
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic MAT tag sequence

<400> SEQUENCE: 36

Cys Gly Gly Gly His Asn His Arg His Lys His
1               5                   10

<210> SEQ ID NO 37
<211> LENGTH: 8
<212> TYPE: PRT
<213> ORGANISM: Artificial Sequence
<220> FEATURE:
<223> OTHER INFORMATION: Synthetic MAT tag sequence

<400> SEQUENCE: 37

His Asn His Arg His Lys His Cys
1               5

<210> SEQ ID NO 38
<211> LENGTH: 8
<212> TYPE: PRT
<213> ORGANISM: Artificial Sequence
```

```
-continued

<220> FEATURE:
<223> OTHER INFORMATION: Synthetic MAT tag sequence

<400> SEQUENCE: 38

Cys His Asn His Arg His Lys His
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic MAT tag sequence

<400> SEQUENCE: 39

His Asn His Arg His Lys His
1               5

<210> SEQ ID NO 40
<211> LENGTH: 24
<212> TYPE: PRT
<213> ORGANISM: Artificial Sequence
<220> FEATURE:
<223> OTHER INFORMATION: Synthetic triple XPRESS Peptide
<220> FEATURE:
<221> NAME/KEY: MISC_FEATURE
<222> LOCATION: (24)..(24)
<223> OTHER INFORMATION: X = a hydrogen or a covalent bond

<400> SEQUENCE: 40

Met Asp Leu Tyr Asp His Asp Gly Asp Leu Tyr Asp His Asp Ile Asp
1               5                   10                  15

Leu Tyr Asp Asp Asp Asp Lys Xaa
            20

<210> SEQ ID NO 41
<211> LENGTH: 22
<212> TYPE: PRT
<213> ORGANISM: Artificial Sequence
<220> FEATURE:
<223> OTHER INFORMATION: synthetic 3X FLAG sequence

<400> SEQUENCE: 41

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic triple XPRESS Peptide

<400> SEQUENCE: 42

Asp Leu Tyr Asp His Asp Gly Asp Leu Tyr Asp His Asp Ile Asp Leu
1               5                   10                  15

Tyr Asp Asp Asp Asp Lys
            20
```

US 7,741,053 B2

PROCESSES FOR PURIFICATION OF RECOMBINANT PROTEINS

FIELD OF THE INVENTION

This invention generally relates to the detection and purification or peptides and proteins. In particular, the processes of the present invention relate to the detection and purification of peptides and proteins comprising a metal ion-affinity peptide having a high affinity for coordinated metals and also being highly antigenic.

BACKGROUND OF THE INVENTION

The possibility of preparing hybrid genes by gene technology has opened up new routes for the analysis of recombinant proteins. By linking the coding gene sequence of a desired protein to the coding gene sequence of a protein fragment having a high affinity for a ligand or antibody (affinity peptide), it is possible to purify desired recombinant proteins in the form of fusion proteins in one step using the affinity peptide.

Immobilized metal affinity chromatography (IMAC), also known as metal chelate affinity chromatography (MCAC), is a specialized aspect of affinity chromatography. The principle behind IMAC lies in the fact that many transition metal ions, e.g., nickel, zinc and copper, can coordinate to the amino acids histidine, cysteine, and tryptophan via electron donor groups on the amino acid side chains. To utilize this interaction for chromatographic purposes, the metal ion is typically immobilized onto an insoluble support. This can be done by attaching a chelating group to the chromatographic matrix. Most importantly, to be useful, the metal of choice must have a higher affinity for the matrix than for the compounds to be purified.

In U.S. Pat. No. 4,569,794, Smith et al. disclose the preparation of a fusion protein containing a metal ion-affinity peptide linker and a biologically active polypeptide, expressing the fusion protein, and purifying it using immobilized metal ion chromatography. Because essentially any biologically active polypeptide could be used, this approach enabled the convenient expression and purification of essentially biologically active polypeptide by immobilized metal ion chromatography.

In U.S. Pat. Nos. 5,310,663 and 5,284,933, Dobeli et al. disclose a process for separating a biologically active polypeptide from impurities by producing the desired polypeptide as a fusion protein containing a metal ion-affinity peptide linker comprising 2 to 6 adjacent histidine residues. Although Dobeli et al.'s metal ion-affinity peptide provides greater metal affinity relative to certain of the sequences disclosed by Smith et al., there is some cautionary evidence that proteins containing His-tags may differ from their wild-type counterparts in dimerization/oligomerization properties. For example, Wu and Filutowicz present evidence that the biochemical properties of the pi(30.5) protein of plasmid R6K, a DNA binding protein, were fundamentally altered due to the presence of an N-terminal 6xHis-tag. Wu, J. and Filutowicz, M., *Acta Biochim. Pol.*, 46: 591-599 (1999). In addition, Rodriguez-Viciana et al. stated that V12 Ras proteins expressed as histidine-tagged fusion proteins exhibited poor biological activity. Rodriguez-Viciana, P., et al., *Cell,* 89: 457-67 (1997).

Antibodies specific for peptides may also be used to detect and purify proteins of interest. Typically, a protein of interest, or target protein, will be expressed in a host cell as a fusion protein comprising both the target protein and an antigenic domain, sometimes referred to as a tag, to which the specific antibodies will attach. The fusion protein can then be detected and purified according to well known methods in the art, such as, for example, Western blot and immunoprecipitation.

In U.S. Pat. No. 4,703,004, Hopp et al. disclose a hybrid polypeptide comprising an antigenic identification peptide and a peptide of interest, as well as nucleic acid sequences encoding the same. This hybrid polypeptide, once expressed, may be detected and purified by chromatographic techniques utilizing an immobilized antibody raised against the antigenic region of the identification polypeptide. This approach enabled the convenient expression and purification of any number of proteins by affinity techniques.

In U.S. Patent Publication No. US 2002-0045193 A1, Brizzard et. al. disclose an identification polypeptide comprising a tandem of antigenic domains and a linking sequence comprising a single cleavage sequence that is not present in the antigenic tandem. This approach provided a peptide tag having increased avidity as a result of the tandem of antigenic domains that could be cleaved from a fusion protein to produce a single target peptide product free of all antigenic domains of the tandem.

While both the metal ion-affinity peptide tags and the antibody based peptide tags have proved to be useful individually, there has yet to have been a tag having the properties of both practical metal affinity and practical antigenicity. Specifically, the metal ion-affinity peptides are generally not antigenic, as demonstrated by the use of antibodies raised against the polyhistidine metal ion-affinity peptides of U.S. Pat. Nos. 5,310,663 and 5,284,933. Methods of detecting and purifying such peptides based upon the use of anti-polyhistidine antibodies typically has resulted in non-specific binding or weak binding to the polyhistidine epitope. Likewise, methods of detecting and purifying hybrid polypeptides such as those disclosed in U.S. Pat. No. 4,703,004 by IMAC or MCAC have also proved to be less than ideal.

SUMMARY OF THE INVENTION

One aspect of the invention is an antibody that binds to a peptide which is relatively hydrophilic, is capable of exhibiting appropriate biological activity, and has a relatively high affinity for coordinating metals. Advantageously, this metal ion-affinity peptide may be incorporated into a fusion peptide or protein to enable ready purification of the fusion peptide or protein from aqueous solutions by immobilized metal affinity chromatography. In addition to the metal ion-affinity peptide, the fusion peptide or protein typically comprises a polypeptide or protein of interest, covalently linked, directly or indirectly, to the metal ion-affinity peptide.

Briefly, therefore, the present invention is directed to an antibody that binds to a polypeptide, protein, or protein fragment represented by the formula $R_1$-$Sp_1$-(His-$Z_1$-His-Arg-His-$Z_2$-His)-$Sp_2$-$R_2$, wherein (His-$Z_1$-His-Arg-His-$Z_2$-His) is a metal ion-affinity peptide, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue, $Z_1$ is an amino acid residue selected from the group consisting of Ala, Arg, Asn, Asp, Gln, Glu, Ile, Lys, Phe, Pro, Ser, Thr, Trp, and Val; and $Z_2$ is an amino acid residue selected from the group consisting of Ala, Arg, Asn, Asp, Cys, Gln, Glu, Gly, Ile, Leu, Lys, Met, Pro, Ser, Thr, Tyr, and Val.

Another aspect of the invention is directed to an antibody that binds to a polypeptide, protein, or protein fragment represented by the formula $R_1$-$Sp_1$-(His-$Z_1$-His-Arg-His-$Z_2$-

His)$_t$-Sp$_2$-R$_2$, wherein (His-Z$_1$-His-Arg-His-Z$_2$-His) is a metal ion-affinity peptide, t is at least 2, R$_1$ is hydrogen, a polypeptide, protein or protein fragment, Sp$_1$ is a covalent bond or a spacer comprising at least one amino acid residue, R$_2$ is hydrogen, a polypeptide, protein or protein fragment, Sp$_2$ is a covalent bond or a spacer comprising at least one amino acid residue, Z$_1$ is an amino acid residue selected from the group consisting of Ala, Arg, Asn, Asp, Gln, Glu, Ile, Lys, Phe, Pro, Ser, Thr, Trp, and Val, and Z$_2$ is an amino acid residue selected from the group consisting of Ala, Arg, Asn, Asp, Cys, Gln, Glu, Gly, Ile, Leu, Lys, Met, Pro, Ser, Thr, Tyr, and Val.

Another aspect of the present invention is an antibody that binds to a polypeptide, protein, or protein fragment represented by the formula R$_1$-Sp$_1$-[(His-Z$_1$-His-Arg-His-Z$_2$-His)-Sp$_2$]$_t$-R$_2$, wherein (His-Z$_1$-His-Arg-His-Z$_2$-His) is a metal ion-affinity peptide, t is at least 2, R$_1$ is hydrogen, a polypeptide, protein or protein fragment, Sp$_1$ is a covalent bond or a spacer comprising at least one amino acid residue, R$_2$ is hydrogen, a polypeptide, protein or protein fragment, Sp$_2$ is a covalent bond or a spacer comprising at least one amino acid residue, Z$_1$ is an amino acid residue selected from the group consisting of Ala, Arg, Asn, Asp, Gln, Glu, Ile, Lys, Phe, Pro, Ser, Thr, Trp, and Val, and Z$_2$ is an amino acid residue selected from the group consisting of Ala, Arg, Asn, Asp, Cys, Gln, Glu, Gly, Ile, Leu, Lys, Met, Pro, Ser, Thr, Tyr, and Val; and each Sp$_2$ of the recombinant polypeptides, proteins or protein fragments may be the same or different.

Another aspect of the present invention is a process for detecting, identifying, isolating, capturing and/or purifying a polypeptide, protein or protein fragment. The process generally comprises combining an antibody capable of binding to a fusion peptide or protein comprising a metal ion-affinity peptide, with a sample, which is typically a liquid mixture, to bind the polypeptide, protein or protein fragment. The process may additionally comprise combining the polypeptide, protein, or protein fragment with an immobilized metal ion.

The present invention, therefore, is further directed to a process for detecting, identifying, isolating, capturing and/or purifying a polypeptide, protein, or protein fragment in or from a sample, the process comprising combining an antibody with the sample to bind a polypeptide, protein or protein fragment described herein to the antibody. Generally, the protein or polypeptide is a recombinant protein or polypeptide and comprises a metal ion-affinity peptide having the sequence His-Z$_1$-His-Arg-His-Z$_2$-His, where Z$_1$ and Z$_2$ are as previously defined. The sample or mixture may optionally be combined with a solid support having antibodies to bind the recombinant protein or polypeptide, a solid support having immobilized metal ions to bind the protein or polypeptide, or a combination of both, and eluting the fusion protein from the solid support.

The present invention is further directed to a kit for the expression and/or separation of the recombinant proteins or polypeptides from a mixture wherein the recombinant proteins or polypeptides contain the sequence R$_1$-Sp$_1$-(His-Z$_1$-His-Arg-His-Z$_2$-His)-Sp$_2$-R$_2$, and R$_1$, R$_2$, Sp$_1$, Sp$_2$, Z$_1$ and Z$_2$ are as previously defined. The kit may comprise, in separate containers, the nucleic acid components to be assembled into a vector encoding for a fusion protein comprising a protein or polypeptide covalently operably linked directly or indirectly to an immobilized metal ion-affinity peptide. In addition, or alternatively, the kit may be comprised of one or more of the following: buffers, enzymes, a chromatography column comprising a resin containing immobilized metal ions or antibodies to the metal affinity-ion peptide, and an instructional brochure explaining how to use the kit.

Other objects and advantages of the present invention will become apparent as the detailed description of the invention proceeds.

BRIEF DESCRIPTION OF THE DRAWINGS

FIG. 2. depicts the results of the study carried out in Example 14. Full-length FLAG-BAP-MAT fusion protein is detected on Western blots by monoclonal antibodies to the FLAG and MAT tags. Lysates from uninduced (lanes 2 and 4) and induced (lanes 3 and 6) *E. coli* cultures and ColorBurst Markers (lanes 1 and 4) were separated by SDS-PAGE and blotted to nitrocellulose. The resulting blot was immunostained using either ANTI-FLAG M2-HRP conjugate (lanes 1-3) or Anti-MAT monoclonal antibody (0.5 µg/ml) followed by Rabbit-Anti-Mouse IgG-HRP conjugate (lanes 4-6). The blots were developed and visualized with TMB Substrate.

DETAILED DESCRIPTION OF THE PREFERRED EMBODIMENTS

Figure 1:
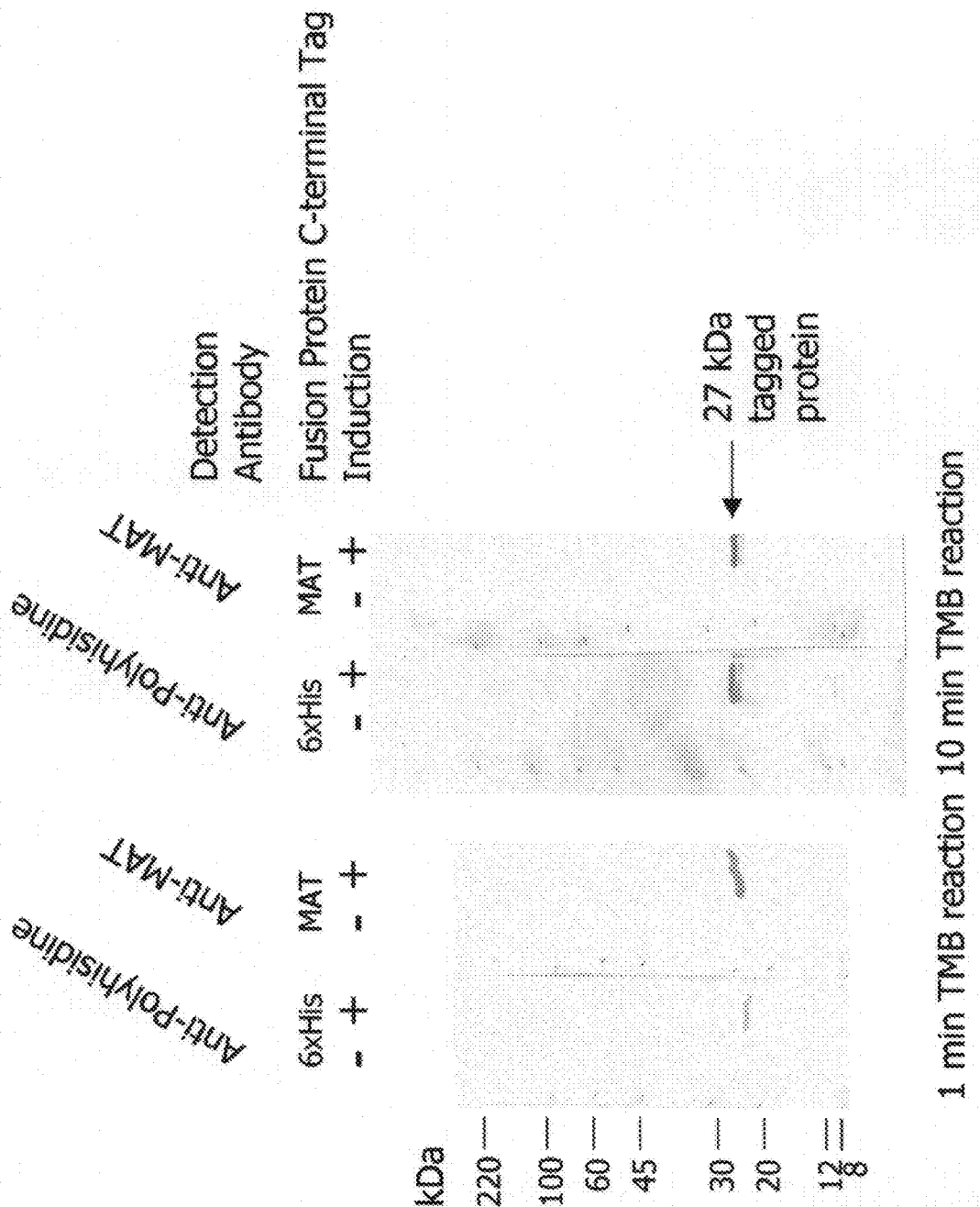
FIG. 1. depicts the results of the study carried out in Example 13 comparing the anti-polyhistidine and anti-MAT monoclonal antibodies for Western blot immunostaining.

The present invention generally relates to processes for identifying, detecting, isolating, purifying, and/or capturing recombinant polypeptides, proteins or protein fragments containing a metal ion-affinity peptide (sometimes referred to as a fusion peptide or fusion protein). Generally, this process comprises contacting a sample or liquid mixture comprising the recombinant protein or polypeptide, wherein the recombinant protein or polypeptide comprises a metal ion-affinity peptide having the sequence His-Z$_1$-His-Arg-His-Z$_2$-His, Z$_1$ and Z$_2$ being defined below, with a solid support having immobilized metal ions to bind the recombinant protein or polypeptide. The process may further comprise eluting the recombinant protein or polypeptide or a fragment thereof from the solid support. Often, the target polypeptide, protein, or protein fragment is a biologically active protein or protein fragment.

Alternatively, the recombinant protein or polypeptide may be identified, detected, isolated, captured, and/or purified by utilizing antibodies that bind to the recombinant protein or polypeptide. Specifically, it has been discovered that particular metal ion-affinity peptides, sometimes referred to as metal affinity tags (MAT or MAT tags), not only demonstrate practical metal affinity, but also demonstrate practical antigenicity. Advantageously, and in contrast to the anti-polyhistidine antibodies discussed previously, the anti-MAT antibodies of the present invention are highly specific for metal ion-affinity peptides, producing a strong specific staining signal and a very low non-specific background staining signal when used, for example, in Western blot immunostaining. This, therefore, readily enables the detection and identification of MAT-tagged polypeptides and proteins by Western blot and cellular immunostaining and the isolation, capture, and/or purification of the same by affinity chromatography and immunoprecipitation/affinity-pull down applications as further described below and as well known in the art. Because the MAT tags also demonstrate metal affinity, this characteristic can also be exploited as an alternative to or in conjunction with the antigenic properties of the MAT tags to alternatively or further detect, identify, isolate, capture, and/or purify such recombinant proteins or polypeptides.

The MAT Antibodies

The antibodies of the present invention bind to metal ion-affinity tags, and in particular metal ion-affinity tags having the peptide sequence characteristics described below. These antibodies may be either monoclonal or polyclonal antibodies, and may be either unpurified (e.g., obtained directly from the immunized animal in the form of ascites, serum or antisera solutions) or purified (e.g., via protein A chromatography). They may also be antibody variants, such as for example, single-chain antibodies (ScFvs or ScFv antibodies); immunologically active fragments of antibodies; proteolytically cleaved antibody fragments, such as for example, Fab fragments (Fab, Fab', and F(ab')$_2$ fragments) and Fc fragments; genetically engineered antibodies, and humanized chimeric antibodies. Such examples are well known in the art, as demonstrated in U.S. Pat. No. 6,193,966, the content of which is hereby incorporated herein by reference.

The antibodies may be used to detect, identify, isolate, capture, and/or purify fusion peptides and proteins containing a metal ion-affinity peptide and prepared by recombinant DNA methodology. In order to obtain such fusion peptides or proteins, typically a gene sequence coding for a desired protein is isolated, synthesized or otherwise obtained and operably linked to a DNA sequence coding for the metal ion-affinity peptide. The hybrid gene containing the gene for a desired protein operably linked to a DNA sequence encoding the metal ion-affinity peptide is referred to as a chimeric gene.

The metal ion-affinity peptide may be covalently linked to the carboxy terminus of the target polypeptide, protein, or protein fragment. It may also be covalently linked to the amino terminus of the target polypeptide, protein, or protein fragment. In either embodiment, the metal ion-affinity peptide and the target polypeptide, protein, or protein fragment may be directly attached by means of a peptide bond or, alternatively, the two may be separated by a linker. When present, the linker may provide other functionality to the recombinant polypeptide, protein, or protein fragment. The antibodies of the present invention are able to bind all such forms of these fusion peptides or proteins.

Accordingly, the antibodies of the present invention bind to recombinant polypeptides, proteins or protein fragments defined by the general formula (I):

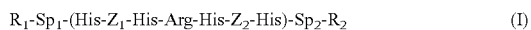

$$R_1\text{-}Sp_1\text{-}(His\text{-}Z_1\text{-}His\text{-}Arg\text{-}His\text{-}Z_2\text{-}His)\text{-}Sp_2\text{-}R_2 \quad (I)$$

wherein (His-$Z_1$-His-Arg-His-$Z_2$-His) is a metal ion-affinity peptide; $Z_1$ is an amino acid residue selected from the group consisting of Ala, Arg, Asn, Asp, Gln, Glu, Ile, Lys, Phe, Pro, Ser, Thr, Trp, and Val; and $Z_2$ is an amino acid residue selected from the group consisting of Ala, Arg, Asn, Asp, Cys, Gln, Glu, Gly, Ile, Leu, Lys, Met, Pro, Ser, Thr, Tyr and Val. In addition, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue. Thus, for example, $R_1$ or $R_2$ may comprise a target polypeptide, protein, or protein fragment which is directly or indirectly linked to the metal ion-affinity peptide.

Accordingly, in one embodiment, the antibodies of the present invention bind to a recombinant polypeptide, protein, or protein fragment defined by formula (I), wherein $Z_1$ is an amino acid selected from the group consisting of Ala, Asn, Ile, Lys, Phe, Ser, Thr, and Val; and $Z_2$ is an amino acid selected from the group consisting of Ala, Asn, Gly, Lys, Ser, Thr, Tyr; and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the antibodies of the present invention bind to a recombinant polypeptide, protein, or protein fragment defined by formula (I), wherein $Z_1$ is an amino acid selected from the group consisting of Asn and Lys; and $Z_2$ is an amino acid selected from the group consisting of Gly and Lys; and $R_1$, $R_2$, $Sp_1$, and $Sp_2$ are as previously defined. For example, in one such embodiment, the recombinant polypeptide, protein or protein fragment is defined by formula (I) wherein $Z_1$ is Asn, $Z_2$ is Lys and $R_1$, $R_2$ $Sp_1$, and $Sp_2$ are as previously defined. By way of further example, in another such embodiment, the recombinant polypeptide, protein or protein fragment is defined by formula (I) wherein $Z_1$ is Lys and $Z_2$ is Gly. In each of these alternatives, the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the antibodies of the present invention bind to a recombinant polypeptide, protein, or protein fragment defined by formula (I), wherein $Z_1$ is Ile, $Z_2$ is Asn, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the antibodies of the present invention bind to a recombinant polypeptide, protein, or protein fragment defined by formula (I), wherein $Z_1$ is Thr, $Z_2$ is Ser, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the antibodies of the present invention bind to a recombinant polypeptide, protein, or protein fragment defined by formula (I), wherein $Z_1$ is Ser, $Z_2$ is Tyr, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues)

regardless of whether the target polypeptide, protein or protein fragment is fused to the amino or carboxy terminus of the metal ion-affinity polypeptide.

In another embodiment, the antibodies of the present invention bind to a recombinant polypeptide, protein, or protein fragment defined by formula (I), wherein $Z_1$ is Val, $Z_2$ is Ala, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the antibodies of the present invention bind to a recombinant polypeptide, protein, or protein fragment defined by formula (I), wherein $Z_1$ is Ala, $Z_2$ is Lys, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In a further embodiment, $R_1$ may be a polypeptide which drives expression of the fusion protein and $R_2$ is the target polypeptide, protein, or protein fragment. In this embodiment, each of $Sp_1$ and $Sp_2$ may be a covalent bond or a spacer, independently of the other. Thus, for example, $R_1$ may be directly fused to the metal ion-affinity peptide or separated from the metal ion-affinity peptide by a spacer independently of whether $R_2$ is directly fused to the metal ion-affinity peptide or separated from the metal ion-affinity peptide by a spacer; all of these combinations and permutations are contemplated. This type of arrangement is particularly useful when chimeric proteins are constructed which comprise epitopes from two portions of antigenic protein or from two different antigenic proteins. Such chimeric proteins may be useful in vaccine preparations.

In another embodiment, the antibodies of the present invention bind to recombinant polypeptides, proteins, or protein fragments comprising multiple copies of the metal ion-affinity peptide (His-$Z_1$-His-Arg-His-$Z_2$-His) wherein $Z_1$ and $Z_2$ are as previously defined. In this embodiment, the additional copies of the metal affinity peptide may occur in either or both of the spacer domains ($Sp_1$ and $Sp_2$) or in either or both of the other domains ($R_1$ and $R_2$) of the recombinant polypeptides, proteins or protein fragments. Thus, for example, in one embodiment a second copy of the metal ion-affinity peptide (His-$Z_1$-His-Arg-His-$Z_2$-His) wherein $Z_1$ and $Z_2$ are as previously defined is located in one of the spacer domains ($Sp_1$ or $Sp_2$) or other domains ($R_1$ and $R_2$) of the recombinant polypeptides, proteins or protein fragments. By way of further example, in another embodiment two additional copies of the metal ion-affinity peptide (His-$Z_1$-His-Arg-His-$Z_2$-His) wherein $Z_1$ and $Z_2$ are as previously defined are located in the spacer domains ($Sp_1$ or $Sp_2$) or other domains ($R_1$ and $R_2$) of the recombinant polypeptides, proteins or protein fragments. By way of further example, in another embodiment at least three additional copies of the metal ion-affinity peptide (His-$Z_1$-His-Arg-His-$Z_2$-His) wherein $Z_1$ and $Z_2$ are as previously defined are located in the spacer domains ($Sp_1$ or $Sp_2$) or other domains ($R_1$ and $R_2$) of the recombinant polypeptides, proteins or protein fragments. In each of these embodiments, the multiple copies of the metal ion-affinity peptide may be separated by one or more amino acid residues (i.e., a spacer) as described herein. Alternatively, in each of these embodiments the multiple copies of the metal ion-affinity peptide may be directly linked to each other without any intervening amino acid residues.

Thus, for example, in one such embodiment the antibodies of the present invention bind to recombinant polypeptides, proteins, or protein fragments defined by the general formula (II):

$$R_1\text{-}Sp_1\text{-}(His\text{-}Z_1\text{-}His\text{-}Arg\text{-}His\text{-}Z_2\text{-}His)_t\text{-}Sp_2\text{-}R_2 \qquad (II)$$

wherein (His-$Z_1$-His-Arg-His-$Z_2$-His) is a metal ion-affinity peptide; t is at least 2 and $R_1$, $R_2$, $Z_1$, $Z_2$, $Sp_1$ and $Sp_2$ are as previously defined. By way of further example, in one such embodiment the antibodies of the present invention bind to recombinant polypeptides, proteins or protein fragments defined by the general formula (III):

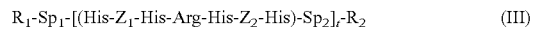

$$R_1\text{-}Sp_1\text{-}[(His\text{-}Z_1\text{-}His\text{-}Arg\text{-}His\text{-}Z_2\text{-}His)\text{-}Sp_2]_t\text{-}R_2 \qquad (III)$$

wherein (His-$Z_1$-His-Arg-His-$Z_2$-His) is a metal ion-affinity peptide; t is at least 2 and $R_1$, $R_2$, $Z_1$, $Z_2$, $Sp_1$ and $Sp_2$ are as previously defined; in addition, each $Sp_2$ of the recombinant polypeptides, proteins or protein fragments corresponding to general formula (III) may be the same or different.

In a preferred embodiment, the antibodies of the present invention bind to a metal ion-affinity sequence comprising the sequence HNHRHKHC (SEQ ID NO: 37). In another preferred embodiment, the antibodies of the present invention bind to a metal ion-affinity sequence comprising the sequence HNHRHKHGGGC (SEQ ID NO:35). In still another preferred embodiment, the antibodies of the present invention bind to a metal ion-affinity sequence comprising the sequence CHNHRHKH (SEQ ID NO: 38). In yet another preferred embodiment, the antibodies of the present invention bind to a metal ion-affinity sequence comprising the sequence CGGGHNHRHKH (SEQ ID NO: 36). In even another preferred embodiment, the antibodies of the present invention bind to a metal ion-affinity sequence comprising the sequence HNHRHKH (SEQ ID NO: 39).

Production of the MAT Antibodies

Polyclonal antibodies may be readily generated by one of ordinary skill in the art from a variety of warm-blooded animals such as horses, cows, various fowl, rabbits, mice, or rats. Briefly, metal ion-affinity peptides are utilized to immunize the animal through intraperitoneal, intramuscular, intraocular, or subcutaneous injections, with an adjuvant such as Freund's complete or incomplete adjuvant. Additional booster immunizations may also be performed. Samples of serum are collected and tested for reactivity to the metal ion-affinity peptide used to immunize the animal. Particularly preferred polyclonal antisera will give a signal on one of these assays that is at least three times greater than background. Once the titer of the animal has reached a plateau in terms of its reactivity to the metal ion-affinity peptide, larger quantities of antisera may be readily obtained either by weekly bleedings, or by exsanguinating the animal.

Monoclonal antibody (MAb) technology may be used to obtain MAbs to rapidly and reliably detect and capture polypeptides and proteins containing metal ion-affinity peptides. For example, hybridomas may be produced using spleen cells from mice immunized with a metal ion-affinity peptide. The spleen cells of each immunized mouse are fused with mouse myeloma Sp 2/0 cells, for example using the polyethylene glycol fusion method of Galfre, G. and Milstein, C., *Methods Enzymol.*, 73:346 (1981). Growth of hybridomas, selection in HAT medium, cloning and screening of clones against antigens are carried out using standard methodology (Galfre, G. and Milstein, C., *Methods Enzymol.*, 73:3-46 (1981)).

HAT-selected clones are injected into mice to produce large quantities of MAb in ascites as described by Galfre, G. and Milstein, C., *Methods Enzymol.*, 73:3-46 (1981), which can be purified using protein A column chromatography (Bio-Rad, Hercules, Calif.). MAbs are selected on the basis of their (a) specificity for a metal ion-affinity peptide, (b) high binding affinity, (c) isotype, and (d) stability.

MAbs can be screened or tested for specificity using any of a variety of standard techniques, including Western blotting (Koren, E. et al., *Biochim. Biophys. Acta* 876:91-100 (1986)) and enzyme-linked immunosorbent assay (ELISA) (Koren, E. et al., *Biochim. Biophys. Acta* 876:91-100 (1986)).

Additional methods that may be used to generate monoclonal or polyclonal antibodies are well known in the art, and include for example, the methods disclosed in U.S. Pat. No. 6,193,966 and in Harlow E. & Lane D., Antibody, Cold Spring Harbor Laboratory Press (1988), the content of each of which is hereby incorporated herein by reference.

Examples of metal ion-affinity peptide antibodies include, for example, antibodies that bind to the metal ion-affinity peptides HNHRHKHGGGC (SEQ ID NO: 35), HNHRH-KHC (SEQ ID NO: 37), CGGGHNHRHKH (SEQ ID NO: 36), CHNHRHKH (SEQ ID NO: 38), and HNHRHKH.

Detection, Identification, Isolation, Capture, and Purification of Recombinant Peptides and Proteins Using the MAT Antibodies The binding of the antibodies of the present invention to a fusion peptide or protein comprising a metal ion-affinity peptide allows for the detection, isolation, capture and/or purification of the fusion peptide or protein. Once the antibodies are bound, the antibodies, and therefore, the fusion peptide or protein, can be detected, for example, by simple visualization, isolated, and then purified. Methods of detecting, isolating, and purifying the antibody bound fusion peptide or protein are well known to those of skill in the art For example, Western blotting is a technique used to detect and isolate a fusion peptide or protein comprising a tag. Generally, small quantities of a fusion protein are electrophoresed on a polyacrylamide gel and transferred (by blotting) to a polymer sheet or membrane. The membrane is then incubated with a first antibody, in this instance, an anti-MAT antibody of the present invention, which binds to the tag of the fusion peptide or protein. The membrane containing the antibody-fusion peptide or protein is then incubated with a second labeled antibody specific for the anti-MAT antibody. The tagged fusion peptide or protein may then be detected and visualized by known methods such as autoradiography, colorimetric and chemiluminescent detection.

An example of an affinity technique is the separation of antibody-bound fusion peptides or proteins marked by the anti-MAT antibodies from peptides or proteins which do not express the MAT tag or otherwise were not labeled by the antibodies. One example of a suitable affinity technique includes fluorescence activated cell sorting (FACS). In FACS, a secondary antibody which is tagged with a fluorescence material, such as fluorescein isothiocyanate (FITC), or rhodamine isothiocyanate (RITC), is introduced into a sample containing the antibody-bound fusion peptide or protein. The anti-MAT antibody is attached to the fusion peptide or protein. The secondary antibody binds to the anti-MAT antibody. Fusion peptides or proteins having the secondary antibody will fluoresce and separation may be achieved by a fluorescence activated cell sorter. FACS can be used to separate fusion peptides or proteins expressing a metal ion-affinity peptide and bound by an anti-MAT antibody by using, for example, an appropriate anti-mouse IgG secondary antibody tagged with a fluorescent material. These methods are well known in the art and are commonly used for other antibodies as well, as disclosed and described in Kunz et al., J. Biol. Chem., Vol. 267, pg. 9101 (1992), incorporated herein by reference.

Another affinity technique is immunoprecipitation. Immunoprecipitation employs antibodies raised against a peptide tag to precipitate a fusion peptide or protein comprising the tag from a sample containing the fusion peptide or protein. The use of immunoprecipitation is known to one skilled in the art. See, for example, Molecular Cloning, A Laboratory Manual, 2d Edition, Maniatis, T. et al. eds. (1989) Cold Spring Harbor Press and Antibodies, A Laboratory Manual, Harlow, E. and Lane, D., eds. (1988) Cold Spring Harbor Press. An example of immunoprecipitation is the use of antibodies coupled to beads. The antibodies coupled to the beads can bind directly to the metal ion-affinity tag. Alternatively, the secondary antibodies may be coupled to the beads, and the secondary antibodies can be specific to the anti-MAT antibodies. A method of attaching antibodies to beads is disclosed and described in U.S. Pat. No. 5,011,912, incorporated herein by reference. For example, fusion peptides or proteins expressing a metal ion-affinity tag may be separated from cells which do not express the same by using the anti-MAT antibodies of the present invention which are coupled to beads by means of a hydrazide linkage. Such methods are generally described with respect to the use of the FLAG® peptide in Brizzard et al., BioTechniques, Vol. 16, pg. 730 (1994), hereby incorporated herein by reference. To accomplish separation using this affinity separation technique, a sample containing the fusion peptide or protein having a MAT tag is mixed with beads which are coupled to an anti-MAT antibody. Fusion peptides or proteins expressing a MAT tag will bind to the antibodies coupled to the beads, while peptides or proteins not expressing a MAT tag will not. The proteins or peptides bound to the beads can then be recovered by, for example, centrifugation. Other variation to these techniques are well known in the art.

Another well known affinity technique is to couple a ligand, such as biotin, to antibodies having an affinity for a fusion peptide or protein comprising a MAT tag. For example, the antibodies of the present invention may be coupled to biotin by a hydrazide linkage, and the fusion peptides or proteins comprising a MAT tag may then be separated from peptides or proteins that do not express a MAT tag through the use of avidin or streptavidin attached to magnetic beads. When the sample is placed in a magnetic field only the peptides or proteins expressing a MAT tag will bind to the magnetic beads via the linkage between the anti-MAT antibody and the bonds between, for example, the biotin and avidin. The peptides or proteins attached to the beads can be recovered and the others washed away.

Other methods of detection, identification, isolation, capture, and/or purification of tagged fusion peptides or proteins are well known in the art, as demonstrated in "Principles and Practice of Immunoassay," Price and Newman, eds., Stochton Press (1991), Molecular Cloning, A Laboratory Manual, 3rd Edition, Sambrook et al. eds., Cold Spring Harbor Press (2001) and Antibodies, A Laboratory Manual. Harlow, E. and Lane, D., eds. (1988) Cold Spring Harbor Press.

Accordingly, one embodiment of the present invention is a process for detecting, identifying, isolating, capturing or purifying a polypeptide, protein, or protein fragment in or from a sample, the process comprising combining an antibody as described herein with the sample to bind the polypeptide, protein or protein fragment to the antibody. The antibody may be either mobilized or immobilized and may be labeled or unlabeled. The process may further comprise releasing the polypeptide, protein, protein fragment, or a portion thereof from the antibody.

In another embodiment of the present invention, the process for detecting, identifying, isolating, capturing or purifying a polypeptide, protein, or protein fragment in or from a sample additionally comprises combining the polypeptide, protein, protein fragment, or a portion thereof with an immobilized metal ion. This may occur either before the polypeptide, protein, or protein fragment in or from the sample is combined with an antibody or it may occur after the polypeptide, protein, or protein fragment in or from the sample is combined with an antibody.

In another embodiment of the process for detecting, identifying, isolating, capturing or purifying a polypeptide, protein, or protein fragment in or from a sample, the polypeptide, protein, or protein fragment comprises a first tag, a second tag, and a polypeptide, protein, or protein fragment positioned between the first and second tag, wherein either the first or the second tag is a metal ion-affinity peptide, and the second tag is selected from the group consisting of the amino acid sequence DYKDDDDK (SEQ ID NO: 15), the amino acid sequence DLYDDDDK (SEQ ID NO: 16), the amino acid sequence DYKDHDGDYKDHDIDYKDDDDK (SEQ ID NO: 41), the amino acid sequence DLYDHDGDLYDHDIDLYDDDDK (SEQ ID NO: 42), GST, GFP, HA, and c-myc. In a particular embodiment, the first tag and the second tag are selected from the following combinations: the first tag is DYKDDDDK (SEQ ID NO: 15) and the second tag is a metal ion-affinity peptide; the first tag is DLYDDDDK and the second tag is a metal ion-affinity peptide; the first tag is DYKDHDGDYKDHDIDYKDDDDK (SEQ ID NO: 41) and the second tag is a metal ion-affinity peptide; the first tag is DLYDHDGDLYDHDIDLYDDDDK (SEQ ID NO: 42) and the second tag is a metal ion-affinity peptide; the first tag is GST and the second tag is a metal ion-affinity peptide; the first tag is GFP and the second tag is a metal ion-affinity peptide; the first tag is HA and the second tag is a metal ion-affinity peptide; and the first tag is c-myc and the second tag is a metal ion-affinity peptide. In another embodiment, the first tag and the second tag are selected from the following combinations: the first tag is a metal ion-affinity peptide and the second tag is DYKDDDDK (SEQ ID NO: 15); the first tag is a metal ion-affinity peptide and the second tag is DLYDDDDK; the first tag is a metal ion-affinity peptide and the second tag is DYKDHDGDYKDHDIDYKDDDDK (SEQ ID NO: 41); the first tag is a metal ion-affinity peptide and the second tag is DLYDHDGDLYDHDIDLYDDDDK (SEQ ID NO: 42); the first tag is a metal ion-affinity peptide and the second tag is GST; the first tag is a metal ion-affinity peptide and the second tag is GFP; the first tag is a metal ion-affinity peptide and the second tag is HA; and the first tag is a metal ion-affinity peptide and the second tag is c-myc.

Target Polypeptide, Protein or Protein Fragment

The target polypeptide, protein or protein fragment may be composed of any proteinaceous substance that can be expressed in transformed host cells. Accordingly, the present invention may be beneficially employed to produce substantially any prokaryotic or eukaryotic, simple or conjugated, protein that can be expressed by a vector in a transformed host cell. For example, the target protein may be a) an enzyme, whether oxidoreductase, transferase, hydrolase, lyase, isomerase or ligase;

b) a storage protein, such as ferritin or ovalbumin or a transport protein, such as hemoglobin, serum albumin or ceruloplasmin;

c) a protein that functions in contractile and motile systems such as actin or myosin;

d) any of a class of proteins that serve a protective or defense function, such as the blood protein fibrinogen or a binding protein, such as antibodies or immunoglobulins that bind to and thus neutralize antigens;

e) a hormone such as human Growth Hormone, somatostatin, prolactin, estrone, progesterone, melanocyte, thyrotropin, calcitonin, gonadotropin and insulin;

f) a hormone involved in the immune system, such as interleukin-1, interleukin-2, colony stimulating factor, macrophage-activating factor and interferon;

g) a toxic protein, such as ricin from castor bean or gossypin from cotton linseed;

h) a protein that serves as structural elements such as collagen, elastin, alpha-keratin, glyco-proteins, viral proteins and muco-proteins; or i) a synthetic protein, defined generally as any sequence of amino acids not occurring in nature.

In general, the target polypeptide, protein or protein fragment may be a constituent of the $R_1$ and $R_2$ moieties of the recombinant polypeptides, proteins or protein fragments corresponding to general formulae (I), (II) and (III).

Genes coding for the various types of protein molecules identified above may be obtained from a variety of prokaryotic or eukaryotic sources, such as plant or animal cells or bacteria cells. The genes can be isolated from the chromosome material of these cells or from plasmids of prokaryotic cells by employing standard, well-known techniques. A variety of naturally occurring and synthesized plasmids having genes coding for many different protein molecules are not commercially available from a variety of sources. The desired DNA also can be produced from mRNA by using the enzyme reverse transcriptase. This enzyme permits the synthesis of DNA from an RNA template.

In one embodiment, $R_1$ may be a protein which enhances expression and $R_2$ is the target polypeptide, protein, or protein fragment. It is well known that the presence of some proteins in a cell result in expression of genes. If a chimeric protein contains an active portion of the protein which prompts or enhances expression of the gene encoding it, greater quantities of the protein may be expressed than if it were not present.

Spacers and Linkers and Other Optional Elements

Spacers and Linkers

In one embodiment, the recombinant polypeptide, protein or protein fragment includes a spacer ($Sp_1$ or $Sp_2$) between the metal ion-affinity polypeptide and the target polypeptide, protein or protein fragment. If present, the spacer may simply comprise one or more, e.g., three to ten amino acid residues, separating the metal ion-affinity peptide from the target polypeptide, protein or protein fragment. Alternatively, the spacer may comprise a sequence which imparts other functionality, such as a proteolytic cleavage site, a fusion protein, a secretion sequence (e.g. OmpA or OmpT for *E. coli*, preprotrypsin for mammalian cells, a-factor for yeast, and melittin for insect cells), a leader sequence for cellular targeting, antibody epitopes, or IRES (internal ribosomal entry sequences) sequences.

In one embodiment, the spacer is selected from among hydrophilic amino acids to increase the hydrophilic character of the recombinant polypeptide, protein or protein fragment. Alternatively, the amino acid(s) of the spacer domain may be selected to impart a desired folding to the recombinant polypeptide, protein or protein fragment thereby increasing accessability to one or more regions of the molecule. For example, the spacer domain may comprise glycine residues which results in a protein folding conformation which allows for improved accessibility to antibodies.

In another embodiment, the spacer comprises a cleavage site which consists of a unique amino acid sequence cleavable by use of a sequence-specific proteolytic agent. Such a site would enable the metal ion-affinity polypeptide to be readily cleaved from the target polypeptide, protein or protein fragment by digestion with a proteolytic agent specific for the amino acids of the cleavage site. Alternatively, the metal ion-affinity peptide may be removed from the desired protein by chemical cleavage using methods known to the art.

When present, the cleavable site may be located at the amino or carboxy terminus of the target peptide. Preferably, the cleavable site is immediately adjacent to the desired protein to enable separation of the desired protein from the metal ion-affinity peptide. This cleavable site preferably does not appear in the desired protein. In one embodiment, the cleavable site is located at the amino terminus of the desired protein. If the cleavable site is located at the amino terminus of the desired protein and if there are remaining extraneous amino acids on the desired protein after cleavage with the proteolytic agent, an endopeptidase such as trypsin, clostropain or furin may be utilized to remove these remaining amino acids, thus resulting in a highly purified desired protein. Further examples of proteolytic enzymatic agents useful for cleavage are papain, pepsin, plasmin, thrombin, enterokinase, and the like. Each effects cleavage at a particular amino acid sequence which it recognizes.

Digestion with a proteolytic agent may occur while the fusion protein is still bound to the affinity resin or alternatively, the fusion protein may be eluted from the affinity resin and then digested with the proteolytic agent in order to further purify the desired protein. Preferably, the amino acid sequence of the proteolytic cleavage site is unique, thus minimizing the possibility that the proteolytic agent will cleave the desired protein. In one embodiment, the cleavable site comprises amino acids for an enterokinase, thrombin or a Factor Xa cleavage site.

Enterokinase recognizes several sequences: Asp-Lys; Asp-Asp-Lys; Asp-Asp-Asp-Lys (SEQ ID NO: 25); and Asp-Asp-Asp-Asp-Lys (SEQ ID NO: 26). The only known natural occurrence of Asp-Asp-Asp-Asp-Lys (SEQ ID NO: 26) is in the protein trypsinogen which is a natural substrate for bovine enterokinase and some yeast proteins. As such, by interposing a fragment containing the amino acid sequence Asp-Asp-Asp-Asp-Lys (SEQ ID NO: 26) as a cleavable site between the metal ion-affinity polypeptide and the amino terminus of the target polypeptide, protein or protein fragment, the metal ion-affinity polypeptide can be liberated from the desired protein by use of bovine enterokinase with very little likelihood that this enzyme will cleave any portion of the desired protein itself.

Thrombin cleaves on the carboxy-terminal side of arginine in the following sequence: Leu-Val-Pro-Arg-Gly-X (SEQ ID NO: 27), where X is a non-acidic amino acid. Factor Xa protease (i.e., the activated form of Factor X) cleaves after the Arg in the following sequences: Ile-Glu-Gly-Arg-X (SEQ ID NO:28), Ile-Asp-Gly-Arg-X (SEQ ID NO: 29), and Ala-Glu-Gly-Arg-X (SEQ ID NO: 30), where X is any amino acid except proline or arginine. A fusion protein comprising the 31 amino-terminal residues of the cII protein, a Factor Xa cleavage site and human β-globin was shown to be cleaved by Factor Xa and generate authentic β-globin. A limitation of the Factor Xa-based fusion systems is the fact that Factor Xa has been reported to cleave at arginine residues that are not present within in the Factor Xa recognition sequence. Nagai, K, et al., *Prot. Expr. and Purif.,* 2:372, 1991.

While less preferred, other unique amino acid sequences for other cleavable sites may also be employed in the spacer without departing from the spirit or scope of the present invention. For instance, the spacer may be composed, at least in part, of a pair of basic amino acids, i.e., Arg, His or Lys. This sequence is cleaved by kallikreins, a glandular enzyme. Also, the spacer may be composed, at least in part, of Arg-Gly, since it is known that the enzyme thrombin will cleave after the Arg if this residue is followed by Gly.

Regardless of whether a cleavage site is present, the recombinant polypeptide, protein or protein fragment may comprise an antigenic domain in a spacer region ($Sp_1$ or $Sp_2$). For example, in one embodiment of the present invention, the recombinant polypeptide, protein or protein fragment comprises one or multiple copies of an antigenic domain generally corresponding to the FLAG® (Sigma-Aldrich, St. Louis, Mo.) peptide sequence joined to a linking sequence containing a single enterokinase cleavage site. Such antigenic domains generally correspond to the sequence:

$$X^{20}\text{-}(X^1\text{-}Y\text{-}K\text{-}X^2\text{-}X^3\text{-}D\text{-}X^4)_n\text{-}X^5\text{-}(X^1\text{-}Y\text{-}K\text{-}X^7\text{-}X^8\text{-}D\text{-}X^9\text{-}K)\text{-}X^{21}$$

where:
D, Y and K are their representative amino acids
$X^{20}$ and $X^{21}$ are independently a hydrogen or a covalent bond;
each $X^1$ and $X^4$ is independently a covalent bond or at least one amino acid residue, if other than a covalent bond, preferably at least one amino acid residue selected from the group consisting of aromatic amino acid residues and hydrophilic amino acid residues, more preferably at least one hydrophilic amino acid residue, and still more preferably at least one an aspartate residue;
each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;
$X^5$ is a covalent bond or a spacer domain comprising at least one amino acid, if other than a covalent bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Phe, Pro, Ser, Thr, Trp, Tyr and Val;
$X^9$ is a covalent bond or D; and
n is 0, 1 or 2.

In this embodiment, the amino acid sequence $X^{20}$-$(X^1$-Y-K-$X^2$-$X^3$-D-$X^4)_n$ comprises an antigenic domain -$X^1$-Y-K-$X^2$-$X^3$-D- joined in tandem which are joined to a linking sequence ($X^1$-Y-K-$X^7$-$X^8$-D-$X^9$-K). The antigenic domains may be immediately adjacent to each other when n is at least one and $X^4$ is a covalent bond; optionally, $X^4$ may be a spacer domain interposed between the multiple copies of antigenic domains. The linking sequence contains a single enterokinase cleavable site which is represented by the sequence -$X^7$-$X^3$-D-X-K, where $X^7$ and $X^8$ may be an amino acid residue or a covalent bond and $X^9$ is a covalent bond or an aspartate residue. In one embodiment, each $X^7$, $X^8$ and $X^9$ is independently an aspartate residue thus resulting in the enterokinase cleavable site DDDDK (SEQ ID NO: 26) which is preferably located immediately adjacent to the amino terminus of the target peptide. When n is at least one and $X^5$ is a covalent bond, the multiple copies of antigenic domains may be immediately adjacent to the linking sequence; optionally, $X^5$ may be a spacer domain interposed between the linking sequence and the antigenic domains. When each $X^4$ and $X^5$ is independently a spacer domain, it is preferred that the amino acid residue(s) of each $X^4$ and $X^5$ impart one or more desired properties to the antigenic domain; for example, the amino acids of the spacer domain may be selected to impart a desired folding to the identification polypeptide thereby increasing accessibility to the antibody. In another embodiment, the amino acids of the spacer domain $X^4$ and $X^5$ may be selected to impart a desired affinity characteristic such as a combination of multiple or alternating histidine residues capable of chelating to an immobilized metal ion on a resin or other matrix. Furthermore, these desired properties may be designed into other areas of the identification polypeptide; for example, the amino acids represented by $X^2$ and $X^3$ may be selected to impart a desired peptide folding or a desired affinity characteristic for use in affinity purification.

In another embodiment, the spacer comprises multiple copies of an antigenic domain. For example, in one embodiment the spacer may comprise a linking sequence containing a single enterokinase or other cleavage site, or generally correspond to the sequence:

$$X^{20}\text{-}(D\text{-}Y\text{-}K\text{-}X^2\text{-}X^3\text{-}D)_n\text{-}X^5\text{-}(D\text{-}Y\text{-}K\text{-}X^7\text{-}X^8\text{-}D\text{-}X^9\text{-}K)\text{-}X^{21}$$

where:

D, Y, K are their representative amino acids;

$X^{20}$ and $X^{21}$ are independently a hydrogen or a covalent bond;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a covalent bond or a spacer domain comprising at least one amino acid, if other than a covalent bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

$X^9$ is a covalent bond or an aspartate residue; and n is at least 2.

In this embodiment, the amino acid sequence $X^{20}$-(D-Y-K-$X^2$-$X^3$-D)$_n$ represents the multiple copies of the antigenic domain D-Y-K-$X^2$-$X^3$-D in tandem which are joined to a linking sequence (D-Y-K-$X^7$-$X^8$-D-$X^9$-K). In this embodiment, one antigenic domain is immediately adjacent to another antigenic domain, i.e., no intervening spacer domains, and the multiple copies of the antigenic domain are immediately adjacent to the linking sequence when $X^5$ is a covalent bond. The linking sequence contains a single enterokinase cleavable site which is represented by the sequence -$X^7$-$X^3$-D-$X^9$-K, where $X^7$ and $X^8$ may be a covalent bond or an amino acid residue, preferably an aspartate residue, and $X^9$ is a covalent bond or an aspartate residue. In one embodiment, each $X^7$, $X^8$ and $X^9$ is independently an aspartate residue thus resulting in the enterokinase cleavable site DDDDK (SEQ ID NO: 26) which is preferably adjacent to the amino terminus of the target peptide. Optionally, the multiple copies of the antigenic domain are joined to the linking sequence by a spacer $X^5$ when $X^5$ is at least one amino acid residue. When $X^5$ is a spacer domain, it is preferred that the amino acid residue(s) of $X^5$ impart one or more desired properties to the recombinant polypeptide, protein or protein fragment; for example, the amino acids of the spacer domain may be selected to impart a desired folding to the recombinant polypeptide, protein or protein fragment thereby increasing accessibility to the antibody. In another embodiment, the amino acids of the spacer domain may be selected to impart a desired affinity characteristic such as a combination of multiple or alternating histidine residues capable of chelating to an immobilized metal ion on a resin or other matrix. Furthermore, these desired properties may be designed into other areas of the spacer; for example, the amino acids represented by $X^2$ and $X^3$ may be selected to impart a desired peptide folding or a desired affinity characteristic for use in affinity purification.

When the affinity polypeptide is located at the amino terminus of the target polypeptide, protein or protein fragment, it is often desirable to design the amino acid sequence such that an initiator methionine is present. Accordingly, in one embodiment of the present invention, the recombinant polypeptide, protein or protein fragment comprises multiple copies of an antigenic domain, a linking sequence containing a single enterokinase cleavage site and generally corresponds to the sequence:

$$X^{20}\text{-}X^{10}\text{-}(D\text{-}Y\text{-}K\text{-}X^2\text{-}X^3\text{-}D)_n\text{-}X^5\text{-}(D\text{-}Y\text{-}K\text{-}X^7\text{-}X^8\text{-}D\text{-}X^9\text{-}K)\text{-}X^{21}$$

where:

D, Y, and K are their representative amino acids;

$X^{20}$ and $X^{21}$ are independently a hydrogen or a covalent bond;

$X^{10}$ is a covalent bond or an amino acid, if other than a covalent bond, preferably a methionine residue;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a covalent bond or a spacer domain comprising at least one amino acid, if other than a bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr, and Val;

$X^9$ is a covalent bond or an aspartate residue; and n is at least 2.

In this embodiment, the amino acid sequence $X^{20}$-(D-Y-K-$X^2$-$X^3$-D)$_n$ represents the multiple copies of the antigenic domain D-Y-K-$X^2$-$X^3$-D in tandem which is flanked by a linking sequence (D-Y-K-$X^7$-$X^8$-D-$X^9$-K) and an initiator amino acid $X^{10}$, preferably methionine. The antigenic domain D-Y-K-$X^2$-$X^3$-D with an initiator methionine is recognized by the M5® antibody (Sigma-Aldrich, St. Louis, Mo.). In this embodiment, one antigenic domain is immediately adjacent to another antigenic domain, i.e., no intervening spacer domains, and the multiple copies of the antigenic domain are immediately adjacent to the linking sequence when $X^5$ is a covalent bond. The linking sequence contains an enterokinase cleavable site which is represented by the amino acid sequence -$X^7$-$X^8$-D-$X^9$-K, where $X^7$ and $X^8$ may be a covalent bond or an amino acid residue, preferably an aspartate residue, and $X^9$ is a covalent bond or an aspartate residue. In one embodiment, each $X^7$, $X^8$ and $X^9$ is independently an aspartate residue thus resulting in the enterokinase cleavable site DDDDK (SEQ ID NO: 26) which is preferably adjacent to the amino terminus of the target peptide. Optionally, the multiple copies of the antigenic domain are joined to the linking sequence by a spacer domain $X^5$ when $X^5$ is at least one amino acid residue. When $X^5$ is a spacer domain, it is preferred that the amino acid residue(s) of $X^5$ impart one or more desired properties to the affinity polypeptide; for example, the amino acids of the spacer domain may be selected to impart a desired folding to the recombinant polypeptide, protein or protein fragment thereby increasing accessibility to the antibody. In another embodiment, the amino acids of the spacer domain may be selected to impart a desired affinity characteristic such as a combination of multiple or alternating histidine residues capable of chelating to an immobilized metal ion on a resin or other matrix. Furthermore, these desired properties may be designed into other areas of the affinity polypeptide; for example, the amino acids represented by $X^2$ and $X^3$ may be selected to impart a desired peptide folding or a desired affinity characteristic for use in affinity purification.

In another embodiment of the present invention, the recombinant polypeptide, protein or protein fragment comprises one or more copies of an antigenic sequence, a linking sequence containing a single enterokinase cleavable site and generally corresponds to the sequence:

$X^{20}$-(D-$X^{11}$-Y-$X^{12}$-$X^{13}$)$_n$-$X^{14}$-(D-$X^{11}$-Y-$X^{12}$-$X^{13}$-D-$X^{15}$-K)-$X^{21}$ where:

D, Y and K are their representative amino acids;
$X^{20}$ and $X^{21}$ are independently a hydrogen or a covalent bond;
each $X^{11}$ is a covalent bond or an amino acid, preferably Leu;
each $X^{12}$ is an amino acid, preferably selected from the group consisting of aromatic amino acid residues and hydrophilic amino acid residues, more preferably a hydrophilic amino acid residue, and still more preferably an aspartate residue;
each $X^{13}$ is a covalent bond or at least one amino acid, if other than a covalent bond, preferably selected from the group consisting of aromatic amino acid residues and hydrophilic amino acid residues, more preferably a hydrophilic amino acid residue, and still more preferably an aspartate residue;
$X^{14}$ is a covalent bond or a spacer domain comprising at least one amino acid, if other than a covalent bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;
$X^{15}$ is a covalent bond or an aspartate residue; and
n is at least 0 or at least 1.

In this embodiment, when n is at least 2, the amino acid sequence $X^{20}$-(D-$X^{11}$-Y-$X^{12}$-$X^{13}$)$_n$ constitutes multiple copies of the antigenic domain D-$X^{11}$-Y-$X^{12}$-$X^{13}$ in tandem which are joined to a linking sequence (D-$X^{11}$-Y-$X^{12}$-$X^{13}$-D-$X^{15}$-K). Additionally, one antigenic domain may be immediately adjacent to another antigenic domain, i.e., no intervening spacer domains, and the multiple copies of the antigenic domain may be immediately adjacent to the linking sequence when $X^{14}$ is a covalent bond. The linking sequence contains a single enterokinase cleavable site which is represented by the sequence -$X^{12}$-$X^{13}$-D-$X^{15}$-K where $X^{12}$ and $X^{13}$ may be a covalent bond or an amino acid residue, preferably an aspartate residue, and $X^{15}$ is a covalent bond or an aspartate residue. In one embodiment, each $X^{12}$, $X^{13}$ and $X^{15}$ is independently an aspartate residue thus resulting in the enterokinase cleavable site DDDDK (SEQ ID NO: 26) which is preferably adjacent to the amino terminus of the target peptide. Optionally, when n is at least two, the multiple copies of the antigenic domain are joined to the linking sequence by a spacer $X^{14}$ when $X^{14}$ is at least one amino acid residue. When $X^{14}$ is a spacer domain, it is preferred that the amino acid residue(s) of $X^{14}$ impart one or more desired properties to the recombinant polypeptide, protein or protein fragment; for example, the amino acids of the spacer domain may be selected to impart a desired folding to the recombinant polypeptide, protein or protein fragment thereby increasing accessibility to the antibody. In another embodiment, the amino acids of the spacer domain $X^{14}$ may be selected to impart a desired affinity characteristic such as a combination of multiple or alternating histidine residues capable of chelating to an immobilized metal ion on a resin or other matrix.

When the affinity polypeptide is located at the amino terminus of the target polypeptide, protein or protein fragment, it is often desirable to design the amino acid sequence such that an initiator methionine is present. In another embodiment of the present invention, the recombinant polypeptide, protein or protein fragment comprises one or more copies of an antigenic sequence, a linking sequence containing a single enterokinase cleavable site and generally corresponds to the sequence:

$X^{20}$-$X^{10}$-(D-$X^{11}$-Y-$X^{12}$-$X^{13}$)$_n$-$X^{14}$-(D-$X^{11}$-Y-$X^{12}$-$X^{13}$-D-$X^{15}$-K)-$X^{21}$ where:

D, Y and K are their representative amino acids;
$X^{20}$ and $X^{21}$ are independently a hydrogen or a covalent bond;
$X^{10}$ is a covalent bond or an amino acid, if other than a covalent bond, preferably a methionine residue;
each $X^{11}$ is a covalent bond or an amino acid, preferably Leu;
each $X^{12}$ is an amino acid, preferably selected from the group consisting of aromatic amino acid residues and hydrophilic amino acid residues, more preferably a hydrophilic amino acid residue, and still more preferably an aspartate residue;
each $X^{13}$ is a covalent bond or at least one amino acid, if other than a covalent bond, preferably selected from the group consisting of aromatic amino acid residues and hydrophilic amino acid residues, more preferably a hydrophilic amino acid residue, and still more preferably an aspartate residue;
$X^{14}$ is a covalent bond or a spacer domain comprising at least one amino acid, if other than a covalent bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

$X^{15}$ is a covalent bond or an aspartate residue; and n is at least 0 or at least 1.

In this embodiment, when n is at least 2, the amino acid sequence $X^{20}$-(D-$X^{11}$-Y-$X^{12}$-$X^{13}$)$_n$ constitutes multiple copies of the antigenic domain D-$X^{11}$-Y-$X^{12}$-$X^{13}$ in tandem which are joined to a linking sequence (D-$X^{11}$-Y-$X^{12}$-$X^{13}$-D-$X^{15}$-K). Additionally, one antigenic domain may be immediately adjacent to another antigenic domain, i.e., no intervening spacer domains, and the multiple copies of the antigenic domain may be immediately adjacent to the linking sequence when $X^{14}$ is a covalent bond. The linking sequence contains a single enterokinase cleavable site which is represented by the sequence -$X^{12}$-$X^{13}$-D-$X^{15}$-K where $X^{12}$ and $X^{13}$ may be a covalent bond or an amino acid residue, preferably an aspartate residue, and $X^{15}$ is a covalent bond or an aspartate residue. In one embodiment, each $X^{12}$, $X^{13}$ and $X^{15}$ is independently an aspartate residue thus resulting in the enterokinase cleavable site DDDDK (SEQ ID NO: 26) which is preferably adjacent to the amino terminus of the target peptide. Optionally, when n is at least two, the multiple copies of the antigenic domain are joined to the linking sequence by a spacer $X^{14}$ when $X^{14}$ is at least one amino acid residue. When $X^{14}$ is a spacer domain, it is preferred that the amino acid residue(s) of $X^{14}$ impart one or more desired properties to the recombinant polypeptide, protein or protein fragment; for example, the amino acids of the spacer domain may be selected to impart a desired folding to the recombinant polypeptide, protein or protein fragment thereby increasing accessibility to the antibody. In another embodiment, the amino acids of the spacer domain $X^{14}$ may be selected to impart a desired affinity characteristic such as a combination of multiple or alternating histidine residues capable of chelating to an immobilized metal ion on a resin or other matrix. In a particular embodiment, the amino acid sequence is M-D-L-Y-D-H-D-G-D-L-Y-D-H-D-I-D-L-Y-D-D-D-D-K-$X^{21}$ (SEQ ID NO:40), wherein $X^{21}$ is a hydrogen or a covalent bond. In a particularly preferred embodiment, $X^{21}$ is a hydrogen.

In another embodiment of this invention, a spacer ($Sp_1$ or $Sp_2$) comprises the enzyme glutathione-S-transferase of the parasite helminth *Schistosoma japonicum* (SEQ ID NO: 1). The glutathione-S-transferase may, however, be derived from other species including human and other mammalian glutathione-S-transferase. Proteins expressed as fusions with the enzyme glutathione-S-transferase can be purified under non-denaturing conditions by affinity chromatography on immobilized glutathione. Glutathione-agarose beads have a capacity of at least 8 mg fusion protein/ml swollen beads and can be used several times for different preparations of the same fusion protein. Smith, D. B. and Johnson, K. S., *Gene*, 67:31-40, 1988.

In another embodiment of this invention, a spacer ($Sp_1$ or $Sp_2$) comprises a cellulose binding domain (CBD) (SEQ ID NO: 2). CBD's are found in both bacterial and fungal sources and possess a high affinity for the crystalline form of cellulose. This property has been useful for purification of fusion proteins using a cellulose matrix. Fusion proteins have been attached at both the N- and C-terminus of CBD.

In another embodiment of this invention, a spacer ($Sp_1$ or $Sp_2$) comprises the Maltose Binding Protein (MBP) encoded by the malE gene in *E. coli* (SEQ ID NO: 3). MBP has found utility in the formation of chimeric proteins with eukaryotic proteins for expression in bacterial systems. This system permits expression of soluble fusion proteins that can readily be purified on immobilized amylose resin.

In another embodiment of this invention, a spacer ($Sp_1$ or $Sp_2$) comprises Protein A (SEQ ID NO: 4). Protein A is isolated from *Staphylococcus aureus* and binds to the Fc origin of IgG. Fusion proteins containing the IgG binding domains of Protein A can be affinity purified on IgG resins (e.g., IgG Sepharose 6FF (Pharmacia Biotech). The signal sequence of Protein A is functional in *E. coli*. Fusion proteins using Protein A have shown increased stability when expressed both in the cytoplasm and periplasm in *E. coli*.

In another embodiment of this invention, a spacer ($Sp_1$ or $Sp_2$) comprises Protein G (SEQ ID NO: 5). Protein G is similar to Protein A with the difference being that Protein G binds to human serum albumin in addition to IgG. The major disadvantage is that low pH (for example, less than 3.4) is required to elute the fusion protein.

In another embodiment of this invention, a spacer ($Sp_1$ or $Sp_2$) comprises IgG (SEQ ID NO: 6). Placing the protein of interest on the C-terminal of IgG generates chimeric proteins. This allows purification of the fusion protein using either Protein A or G matrix.

In another embodiment of this invention, a spacer ($Sp_1$ or $Sp_2$) comprises the enzyme chloramphenicol acetyl transferase (CAT) from *E. coli* (SEQ ID NO: 7). CAT is used in the form of a C-terminal fusion. CAT is readily translated in *E. coli* and allows for over-expression of heterologous proteins. Capture of fusion proteins is accomplished using a chloramphenicol matrix.

In another embodiment of this invention, a spacer ($Sp_1$ or $Sp_2$) comprises streptavidin (SEQ ID NO: 8). Streptavidin is used for fusion proteins because of its high affinity and high specificity for biotin. Streptavidin is a neutral protein, free from carbohydrates and sulphydryl groups.

In another embodiment of this invention, a spacer ($Sp_1$ or $Sp_2$) comprises b-galactosidase (SEQ ID NO: 9). β-galactosidase is a enzyme that is utilized as both an N- and C-terminal fusion protein. Fusion proteins containing b-galactosidase sequences can be affinity purified on aminophenyl-β-D-thiogalactosidyl-succinyldiaminohexyl-Sepharose. However, given that C-terminal fusion proteins are usually insoluble, the system has limited use in bacterial systems. N-terminal fusions are soluble in *E. coli*, but due to the large size of b-galactosidase, this system is used more often in eukaryotic gene expression.

In another embodiment of this invention, a spacer ($Sp_1$ or $Sp_2$) comprises the Green Fluorescent Protein (GFP) (SEQ ID NO: 10). GFP is a protein from the jellyfish *Aquorea victorea* and many mutant variations of this protein have been used successfully in most organisms for protein expression. The major use of these types of fusion proteins is for targeting and determining physiological function of the host cell protein.

In another embodiment of this invention, a spacer ($Sp_1$ or $Sp_2$) comprises thioredoxin (SEQ ID NO: 11). Thioredoxin is a relatively small thermostable protein that is easily over-expressed in bacterial systems. Thioredoxin fusion systems are useful in avoiding the formation of inclusion bodies during heterologous gene expression. This has been particularly useful in the expression of mammalian cytokines.

In another embodiment of this invention, a spacer ($Sp_1$ or $Sp_2$) comprises Calmodulin Binding Protein (CBP) (SEQ ID NO: 12). This tag is derived from the C-terminus of skeletal muscle myosin light chain kinase. This small tag is recognized by calmodulin and forms the base of the technology.

The tag is translated efficiently and allows for the expression and recovery of N-terminal chimeric genes.

In another embodiment of this invention, a spacer ($Sp_1$ or $Sp_2$) comprises the c-myc epitope sequence Glu-Gln-Lys-Leu-Ile-Ser-Glu-Glu-Asp-Leu (SEQ ID NO: 13). This C-terminal portion of the myc oncogene, which is part of the p53 signaling pathway, has been used as a detection tag for expression of recombinant proteins in mammalian cells.

In another embodiment of this invention, a spacer ($Sp_1$ or $Sp_2$) comprises the HA epitope sequence Tyr-Pro-Tyr-Asp-Val-Tyr-Ala (SEQ ID NO: 14). This detection tag has been utilized for the expression of recombinant proteins in mammalian cells.

In another embodiment of this invention, the spacer ($Sp_1$ or $Sp_2$) comprises a polypeptide possessing an amino acid sequence having at least 70% homology to any one of the amino acid sequences disclosed in SEQ ID NOS:1-14, and retains the same binding characteristics as said amino acid sequence.

DNA sequences encoding the aforementioned proteins which may be employed as spacers ($Sp_1$ or $Sp_2$) are commercially available (e.g., malE gene sequences encoding the MBP are available from New England Biolabs (pMAL-c2 and pMAL-p2); *Schistosoma japonicum* glutathione-S-transferase (GST) gene sequences are available from Pharmacia Biotech (the pGEX series which have GenBank Accession Nos.: U13849 to U13858); β-galactosidase (the lacZ gene product) gene sequences are available from Pharmacia Biotech (pCH110 and pMC1871; GenBank Accession Nos: U13845 and L08936, respectively); sequences encoding the IgG binding domains of Protein A are available from Pharmacia Biotech (pRIT2T; GenBank Accession No. U13864)).

When any of the above listed proteins (including the hinge/Fc domains of human $IgG_1$) are used as spacers, it is not required that the entire protein be used as a spacer. Portions of these proteins may be used as the spacer provided the portion selected is sufficient to permit interaction of a fusion protein containing the portion of the protein used as the spacer with the desired affinity resin.

Multiple Tags

The antibodies of the present invention may be used in conjunction with other tags, such as those disclosed above with respect to spacers. Examples of such tags include Green Fluorescent Protein (GFP), the FLAG® peptide (DYKD-DDDK [SEQ ID NO: 15]) and variants thereof, the XPRESS™ peptide (DLYDDDDK [SEQ ID NO:16]) and variants thereof, GST, HA, and c-myc. Accordingly, a fusion peptide or protein may contain a tag at only the N-terminus, at only the C-terminus, or at both the N- and C-termini. Likewise, more than one tag may be located at only the N-terminus, at only the C-terminus, or at both the N- and C-termini.

Of particular interest is the use of two different tags, one each at the N-terminus and the C-terminus of a chimeric gene or fusion peptide or protein, wherein one of the two tags is a metal ion-affinity peptide. Such a use of multiple tags allows for a determination as to whether a complete fusion peptide or protein has been expressed from a chimeric gene.

Generally, a fusion peptide or protein may be produced from a chimeric gene by *E. coli* or other bacterial or expression systems. These peptides or proteins may then be isolated, such as for example from a solution, on a chromatography column or via immunoprecipitation. Once isolated, the tag may be removed from the fusion protein, such as for example, by proteolytic cleavage. The end result is a target peptide or protein free of the tag. Isolation and purification of fusion peptides or proteins based upon a single tag, however, does not indicate whether the peptide or protein is the complete intact protein. Accordingly, time and money may be wasted in purifying what ultimately is determined (after purification and other identification procedures) to be an incomplete peptide or non-functional protein.

Therefore, in order to identify whether a desired target peptide or protein was expressed as a single and complete peptide or protein, such a peptide or protein may be labeled at both the N-terminus and C-terminus with different tags, one of which is a metal ion-affinity peptide, thereby allowing for interrogation of the fusion peptide or protein by, for example, Western blot and IMAC or MCAC, to determine if the fusion peptide or protein, and ultimately, therefore, the target peptide or protein, is in a single and complete fusion peptide or protein.

By way of example, and as detailed in Example 14, a chimeric gene comprising a nucleotide sequence encoding the target peptide or protein, a first tag at the N-terminus of the nucleotide sequence, and a second tag at the C-terminus of the nucleotide sequence, wherein either the first or the second tag is a metal ion-affinity peptide, may be inserted into host cell and expressed. Thereafter, the expressed peptide or protein may be harvested, such as for example, by centrifugation, and then lysed. The lysate may then be separated by methods known in the art, such as for example, by SDS-PAGE followed by Western blotting. The tags may then be visualized, such as for example, by immunostaining.

Full length fusion peptides or proteins will be able to be visualized by both tags. Incomplete fusion proteins, whether the result of proteolytic degradation or incomplete transcription or translation, will only be visualized based upon either the first or second tag. Peptides and proteins lacking both tags will not be able to be visualized. As a result, a practitioner will be able to quantitatively determine the amount of full length fusion peptides or proteins that have been expressed and then isolate and further treat only those full length peptides or proteins.

The use of two tags also allows for the detection, identification, isolation, capture, and/or purification of fusion peptides or proteins by more than one method. Specifically, the fusion proteins may be detected, identified, isolated, captured, and/or purified by use of IMAC or MCAC followed by antibody based visualization or affinity techniques. Likewise, the fusion proteins may be detected, identified, isolated, captured, and/or purified by use of antibody based visualization or affinity techniques followed by IMAC or MCAC.

Accordingly, one aspect of the present invention is a process for determining whether an entire fusion peptide or protein has been expressed, said process comprising constructing a chimeric gene comprising a nucleotide sequence encoding the target peptide or protein, a first tag at the N-terminus of the nucleotide sequence, and a second tag at the C-terminus of the nucleotide sequence, wherein either the first or the second tag is a metal ion-affinity peptide, expressing said chimeric gene as a fusion peptide or protein, and visualizing the expressed peptide or protein. In one embodiment, either the first or the second tag is a metal ion-affinity peptide, and the tag that is not a metal ion-affinity peptide is selected from the group consisting of the FLAG® peptide or variants thereof, the XPRESS™ peptide or variants thereof, GFP, GST, HA, and c-myc. As described in this embodiment, the first and second tags are different from one another. Moreover, as described in this embodiment, the metal-ion affinity peptide may be located at either the N- or C-terminus.

Alternatively, there may be instances wherein the use of more than one tag at the N-terminus, at the C-terminus, or at both the N- and C-termini may be advantageous. Accordingly, another embodiment of the invention is a process for labeling a fusion peptide or protein with at least two tags at the N-terminus of the fusion peptide or protein, said process comprising constructing a chimeric gene comprising a nucleotide sequence encoding the target peptide or protein, a first tag at the N-terminus of the nucleotide sequence, and a second tag at the N-terminal end of the nucleotide sequence, said second tag being adjacent to the first tag. The second tag may be either N-terminal or C-terminal to the first tag. In a particular embodiment, the first tag or the second tag is a metal ion-affinity peptide and the other tag is selected from the group consisting of the FLAG® peptide or variants thereof, the XPRESS™ peptide or variants thereof, GFP, GST, HA, and c-myc.

Another embodiment of the invention is a process for labeling a fusion peptide or protein with at least two tags at the C-terminus of the fusion peptide or protein, said process comprising constructing a chimeric gene comprising a nucleotide sequence encoding the target peptide or protein, a first tag at the C-terminus of the nucleotide sequence, and a second tag at the C-terminal end of the nucleotide sequence, said second tag being adjacent to the first tag. The second tag may be either N-terminal or C-terminal to the first tag. In a particular embodiment, the first tag or the second tag is a metal ion affinity peptide and the other tag is selected from the group consisting of the FLAG® peptide or variants thereof, the XPRESS™ peptide or variants thereof, GFP, GST, HA, and c-myc.

Another embodiment of the invention is a process for labeling a fusion peptide or protein with at least two tags at both the N- and C-termini of the fusion peptide or protein, said process comprising constructing a chimeric gene comprising a nucleotide sequence encoding the target peptide or protein, a first tag at the N-terminus of the nucleotide sequence, a second tag at the N-terminal end of the nucleotide sequence, a first tag at the C-terminus of the nucleotide sequence, and a second tag at the C-terminal end of the nucleotide sequence, each second tag being adjacent to its respective first tag. The second tag may be either N-terminal or C-terminal to its respective first tag. In a particular embodiment, at least one of the first or the second tags is a metal ion affinity peptide and the other tags are independently selected from the group consisting of the FLAG® peptide or variants thereof, the XPRESS™ peptide or variants thereof, GFP, GST, HA, c-myc, and a metal ion-affinity peptide.

A cleavage site may be located within the tags themselves, such as for example, the enterokinase cleavage site located within the FLAG® peptide and other peptide sequences discussed in greater detail above. Alternatively, a cleavage site may be inserted between the tags and the target peptide or between the multiple copies of the tags themselves. Such cleavage sites are discussed in greater detail above. In any event, the insertion of such a cleavage site may be achieved by inserting the nucleotide sequence coding for the same in chimeric gene used to express the fusion peptide or protein.

Expression and Purification

The polypeptides, proteins and protein fragments to which the antibodies of the present invention may bind are generally prepared and expressed as a fusion protein using conventional recombinant DNA technology. The fusion protein is thus produced by host cells transformed with the genetic information encoding the fusion protein. The host cells may secrete the fusion protein into the culture media or store it in the cells whereby the cells must be collected and disrupted in order to extract the product. As hosts, E. coli, yeast, insect cells, mammalian cells and plants are suitable. Of these, E. coli will typically be the more preferred host for most applications. In one embodiment, the recombinant polypeptides, proteins and protein fragments are produced in a soluble form or secreted from the host.

In general, a chimeric gene is inserted into an expression vector which allows for the expression of the desired fusion protein in a suitable transformed host. The expression vector provides the inserted chimeric gene with the necessary regulatory sequences to control expression in the suitable transformed host.

There are six elements of control expression sequence for proteins which are to be secreted from a host into the medium, while five of these elements apply to fusion proteins expressed intracellularly. These elements in the order they appear in the gene are: a) the promoter region; b) the 5' untranslated region; c) signal sequence; d) the chimeric coding sequence; e) the 3' untranslated region; f) the transcription termination site. Fusion proteins which are not secreted do not contain c), the signal sequence.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding the metal ion-affinity peptide containing fusion protein or can be introduced on a separate vector. Cells stably transfected with the introduced nucleic acid can be identified by drug selection (e.g., cells that have incorporated the selectable marker gene will survive, while the other cells die). Methods and materials for preparing recombinant vectors, transforming host cells using replicating vectors, and expressing biologically active foreign polypeptides and proteins are generally well known.

The expressed recombinant polypeptides, proteins and protein fragments may be separated from other material present in the secretion media or extraction solution, or from other liquid mixtures, through immobilized metal affinity chromatography ("IMAC"). For example, the culture media containing the secreted recombinant polypeptides, proteins and protein fragments or the cell extracts containing the recombinant polypeptides, proteins and protein fragments may be passed through a column that contains a resin comprising an immobilized metal ion. In IMAC, metal ions are immobilized onto to a solid support, and used to capture proteins comprising a metal chelating peptide. The metal chelating peptide may occur naturally in the protein, or the protein may be a recombinant protein with an affinity tag comprising a metal chelating peptide. Exemplary metal ions include aluminum, cadmium, calcium, cobalt, copper, gallium, iron, nickel, ytterbium and zinc. In one embodiment, the metal ion is preferably nickel, copper, cobalt, or zinc. In another embodiment, the metal ion is nickel. Advantageously, the components of the solution other than recombinant polypeptide, protein or protein fragment freely pass through the column. The immobilized metal, however, chelates or binds the recombinant polypeptides, proteins and protein fragments, thereby separating it from the remaining contents of the liquid mixture in which it was originally contained.

Resins useful for producing immobilized metal ion affinity chromatography (IMAC) columns are available commercially. Examples of resins derivatized with iminodiacetic acid (IDA) are Chelating Sepharose 6B (Pharmacia), Immobilized Iminodiacetic Acid (Pierce), and Iminodiacetic Acid Agarose (Sigma-Aldrich). In addition, Porath has immobilized tris(carboxymethyl)ethylenediamine (TED) on Sepharose 6B and used it to fractionate serum proteins. Porath, J. and Olin, B., *Biochemistry*, 22:1621-1630, 1983. Other reports suggest that trisacryl GF2000 and silica can be derivatized with IDA, TED, or aspartic acid, and the resulting materials used in producing IMAC substances.

In one embodiment, the capture ligand is a metal chelate as described in WO 01/81365. More specifically, in this embodiment the capture ligand is a metal chelate derived from metal chelating composition (1):

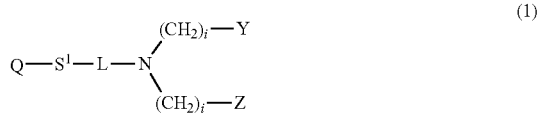

(1)

wherein
Q is a carrier;
$S^1$ is a spacer;
L is -A-T-CH(X)- or —C(=O)—;
A is an ether, thioether, selenoether, or amide linkage;
T is a bond or substituted or unsubstituted alkyl or alkenyl;
X is —$(CH_2)_k CH_3$, —$(CH_2)_k COOH$, —$(CH_2)_k SO_3 H$, —$(CH_2)_k PO_3 H_2$, —$(CH_2)_k N(J)_2$, or —$(CH_2)_k P(J)_2$, preferably —$(CH_2)_k COOH$ or —$(CH_2)_k SO_3 H$;
k is an integer from 0 to 2;
J is hydrocarbyl or substituted hydrocarbyl;
Y is —COOH, —H, —$SO_3 H$, —$PO_3 H_2$, —$N(J)_2$, or —$P(J)_2$, preferably, —COOH;
Z is —COOH, —H, —$SO_3 H$, —$PO_3 H_2$, —$N(J)_2$, or —$P(J)_2$, preferably, —COOH; and
i is an integer from 0 to 4, preferably 1 or 2.

In general, the carrier, Q, may comprise any solid or soluble material or compound capable of being derivatized for coupling. Solid (or insoluble) carriers may be selected from a group including agarose, cellulose, methacrylate co-polymers, polystyrene, polypropylene, paper, polyamide, polyacrylonitrile, polyvinylidene, polysulfone, nitrocellulose, polyester, polyethylene, silica, glass, latex, plastic, gold, iron oxide and polyacrylamide, but may be any insoluble or solid compound able to be derivatized to allow coupling of the remainder of the composition to the carrier, Q. Soluble carriers include proteins, nucleic acids including DNA, RNA, and oligonucleotides, lipids, liposomes, synthetic soluble polymers, proteins, polyamino acids, albumin, antibodies, enzymes, streptavidin, peptides, hormones, chromogenic dyes, fluorescent dyes, flurochromes or any other detection molecule, drugs, small organic compounds, polysaccharides and any other soluble compound able to be derivatized for coupling the remainder of the composition to the carrier, Q. In one embodiment, the carrier, Q, is the container of the present invention. In another embodiment, the carrier, Q, is a body provided within the container of the present invention.

The spacer, $S^1$, which flanks the carrier comprises a chain of atoms which may be saturated or unsaturated, substituted or unsubstituted, linear or cyclic, or straight or branched. Typically, the chain of atoms defining the spacer, $S^1$, will consist of no more than about 25 atoms; stated another way, the backbone of the spacer will consist of no more than about 25 atoms. More preferably, the chain of atoms defining the spacer, $S^1$, will consist of no more than about 15 atoms, and still more preferably no more than about 12 atoms. The chain of atoms defining the spacer, $S^1$, will typically be selected from the group consisting of carbon, oxygen, nitrogen, sulfur, selenium, silicon and phosphorous and preferably from the group consisting of carbon, oxygen, nitrogen, sulfur and selenium. In addition, the chain atoms may be substituted or unsubstituted with atoms other than hydrogen such as hydroxy, keto (=O), or acyl such as acetyl. Thus, the chain may optionally include one or more ether, thioether, selenoether, amide, or amine linkages between hydrocarbyl or substituted hydrocarbyl regions. Exemplary spacers, $S^1$, include methylene, alkyleneoxy(—$(CH_2)_a O$—), alkylenethioether (—$(CH_2)_a S$—), alkyleneselenoether (—$(CH_2)_a Se$—), alkyleneamide(—$(CH_2)_a NR^1 (C=O)$—), alkylenecarbonyl(—$(CH_2)_a CO$)—, and combinations thereof wherein a is generally from 1 to about 20 and $R^1$ is hydrogen or hydrocarbyl, preferably alkyl. In one embodiment, the spacer, $S^1$, is a hydrophilic, neutral structure and does not contain any amine linkages or substituents or other linkages or substituents which could become electrically charged during the purification of a polypeptide.

As noted above, the linker, L, may be -A-T-CH(X)- or —C(=O)—. When L is -A-T-CH(X)-, the chelating composition corresponds to the formula:

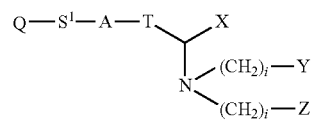

wherein Q, $S^1$, A, T, X, Y, and Z are as previously defined. In this embodiment, the ether (—O—), thioether (—S—), selenoether (—Se—) or amide ((—$NR^1 (C=O)$—) or (—(C=O)$NR^1$—) wherein $R^1$ is hydrogen or hydrocarbyl) linkage is separated from the chelating portion of the molecule by a substituted or unsubstituted alkyl or alkenyl region. If other than a bond, T is preferably substituted or unsubstituted $C_1$ to $C_6$ alkyl or substituted or unsubstituted $C_2$ to $C_6$ alkenyl. More preferably, A is —S—, T is —$(CH_2)_n$—, and n is an integer from 0 to 6, typically 0 to 4, and more typically 0, 1 or 2.

When L is —C(=O)—, the chelating composition corresponds to the formula:

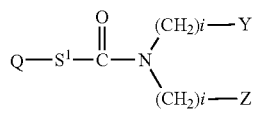

wherein Q, $S^1$, i, Y, and Z are as previously defined.

In one embodiment, the sequence -$S^1$-L-, in combination, is a chain of no more than about 35 atoms selected from the group consisting of carbon, oxygen, sulfur, selenium, nitrogen, silicon and phosphorous, more preferably only carbon, oxygen sulfur and nitrogen, and still more preferably only carbon, oxygen and sulfur. To reduce the prospects for non-specific binding, nitrogen, when present, is preferably in the form of an amide moiety. In addition, if the carbon chain atoms are substituted with anything other than hydrogen, they are preferably substituted with hydroxy or keto. In one embodiment, L comprises a portion (sometimes referred to as a fragment or residue) derived from an amino acid such as cystine, homocystine, cysteine, homocysteine, aspartic acid, cysteic acid or an ester thereof such as the methyl or ethyl ester thereof.

Exemplary chelating compositions corresponding to formula 1 include the following:

1-1
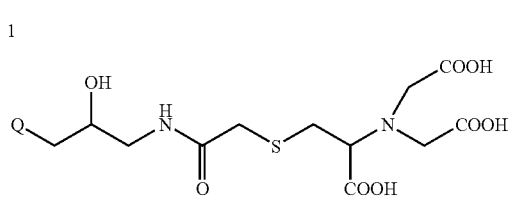

1-2
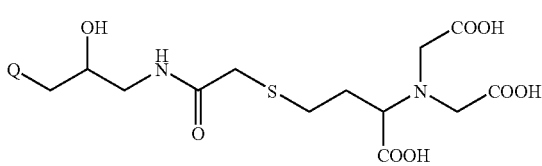

1-3
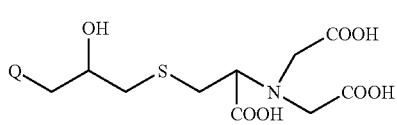

1-4
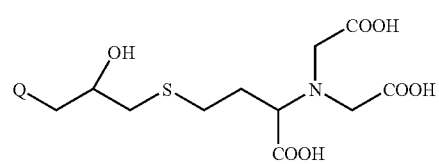

1-5
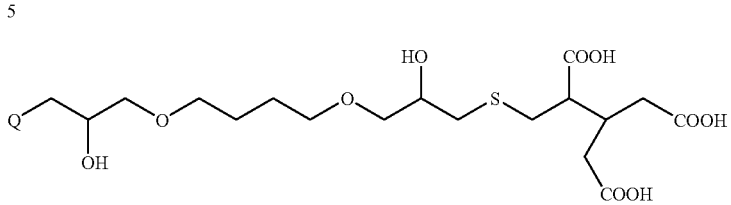

1-6
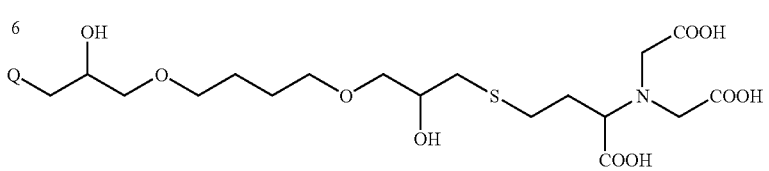

-continued
7
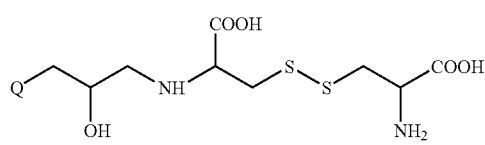
1-7
8
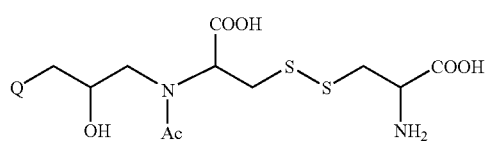
1-8
9
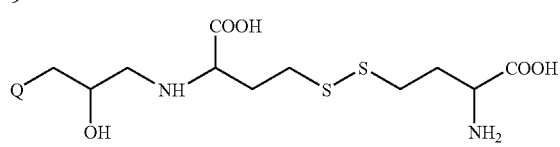
1-9
10
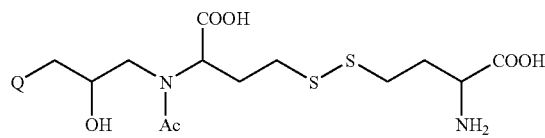
1-10
11
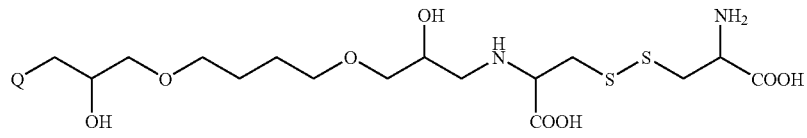
1-11
12
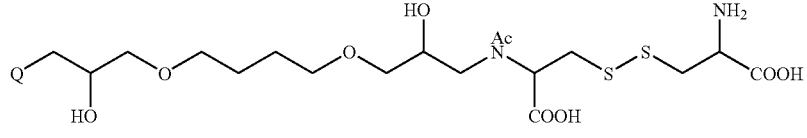
1-12
13
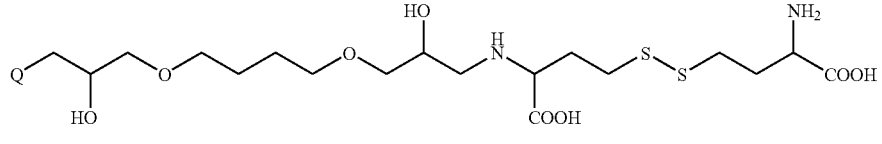
1-13
14
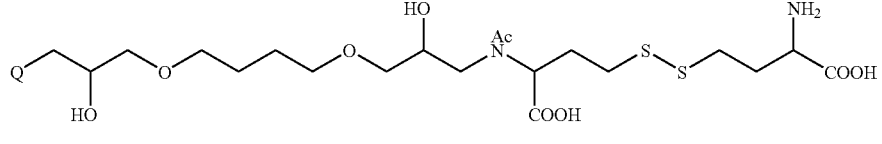
1-14
15
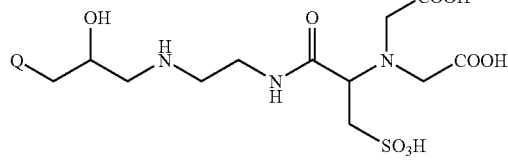
1-15

-continued
16 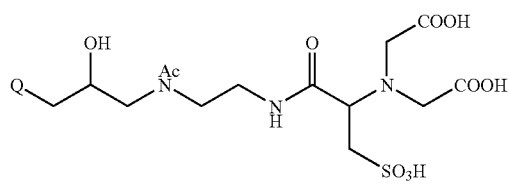 1-16
17 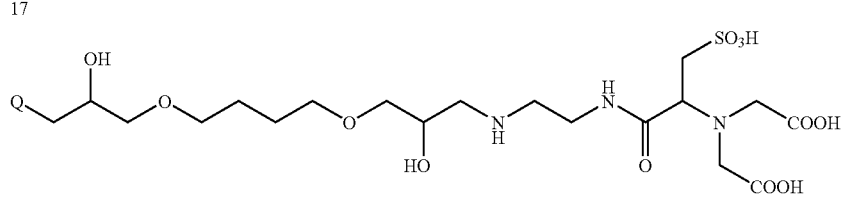 1-17
18 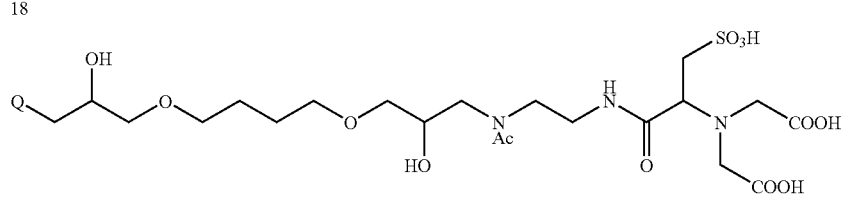 1-18
19 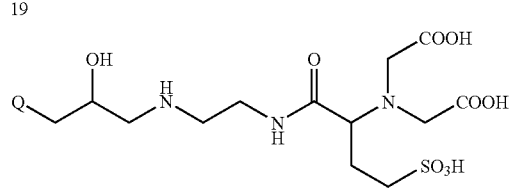 1-19
20 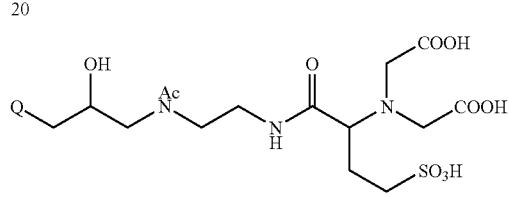 1-20
21 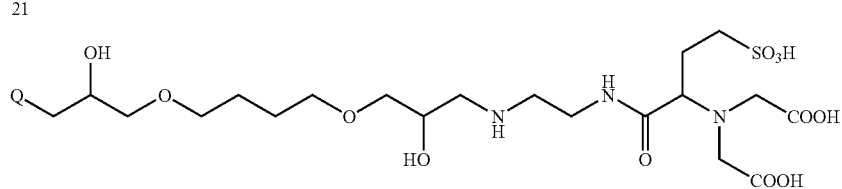 1-21
22 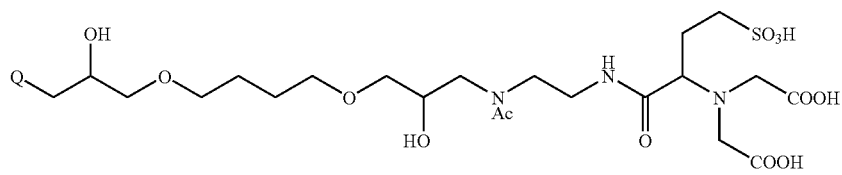 1-22

23
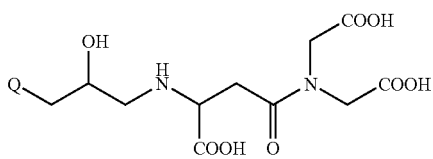
1-23

24
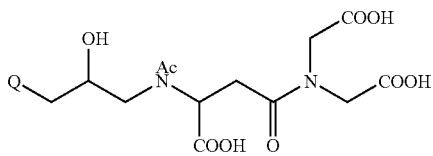
1-24

25
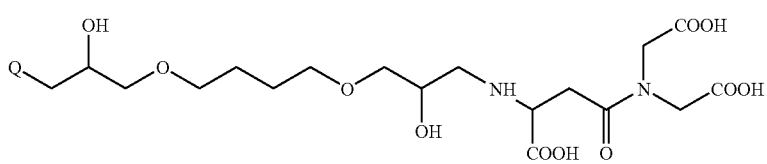
1-25

26
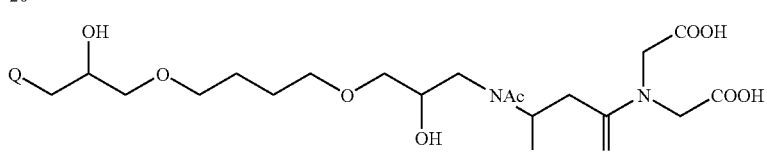
1-26 wherein Q is a carrier and Ac is acetyl.

In another embodiment, the capture ligand is a metal chelate of the type described in U.S. Pat. No. 5,047,513. More specifically, in this embodiment the capture ligand is a metal chelate derived from nitrilotriacetic acid derivatives of the formula

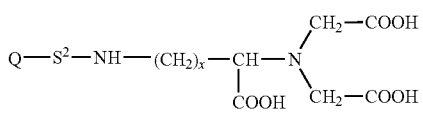

wherein $S^2$ is —O—$CH_2$—CH(OH)—$CH_2$— or —O—CO— and x is 2, 3 or 4. In this embodiment, the nitrilotriacetic acid derivative is immobilized on any of the previously described carriers, Q.

In these embodiments in which the capture ligand is a metal chelate as described in WO 01/81365 or U.S. Pat. No. 5,047,513, the metal chelate may contain any of the metal ions previously described in connection with IMAC. In one embodiment, the metal chelate comprises a metal ion selected from among nickel ($Ni^{2+}$), zinc ($Zn^{2+}$), copper ($Cu^{2+}$), iron ($Fe^{3+}$), cobalt ($Co^{2+}$), calcium ($Ca^{2+}$), aluminum ($Al^{3+}$), magnesium ($Mg^{2+}$), and manganese ($Mn^{2+}$). In another embodiment, the metal chelate comprises nickel ($Ni^{2+}$).

Another common purification technique that can be used in the context of the present invention is the use of an immunogenic capture system where the recombinant polypeptide, protein or protein fragment comprises an antigenic domain in a spacer region ($Sp_1$ or $Sp_2$). Any of the previously described antigenic systems comprising the spacer may be used for this purpose. In such systems, an epitope tag on a protein or peptide allows the protein to which it is attached to be purified based upon the affinity of the epitope tag for a corresponding ligand (e.g., antibody) immobilized on a support. One example of such a tag is the sequence Asp-Tyr-Lys-Asp-Asp-Asp-Asp-Lys, or DYKDDDDK (SEQ ID NO:15); antibodies having specificity for this sequence are sold by Sigma-Aldrich (St. Louis, Mo.) under the FLAG® trademark. Another example of such a tag is the sequence Asp-Leu-Tyr-Asp-Asp-Asp-Asp-Lys, or DLYDDDDK (SEQ ID NO:16); antibodies having specificity for this sequence are sold by Invitrogen (Carlsbad, Calif.). Another example of such a tag is the 3× FLAG® sequence Met-Asp-Tyr-Lys-Asp-His-Asp-Gly-Asp-Tyr-Lys-Asp-His-Asp-Ile-Asp-Tyr-Lys-Asp-Asp-Asp-Asp-Lys (SEQ ID NO:17); antibodies having specificity for this sequence are sold by Sigma-Aldrich (St. Louis, Mo.). Thus, in one embodiment, the carrier comprises immobilized antibodies which have specificity for the DYKDDDDK (SEQ ID NO: 15) epitope; in another embodiment, the carrier comprises immobilized antibodies which have specificity for the DLYDDDDK (SEQ ID NO: 16) epitope. In another embodiment, the carrier comprises immobilized antibodies which have specificity for SEQ ID NO: 17. For example, in one embodiment, the ANTI-FLAG® M1, M2, or M5 antibody is immobilized on the interior surface of a column, or a portion thereof, and/or a bead or other support within a column.

After the recombinant polypeptides, proteins and protein fragments are separated from other components of the liquid mixture, the conditions in the column may be changed to release the bound material. For example, the bound molecules may be eluted by pH change, imidazole, or competition with another linker peptide from the column.

Alternatively, the target polypeptide, protein or protein fragment portion of the bound recombinant polypeptide, protein or protein fragment may be selectively released from immobilized metal. For example, if there is a cleavage site between the target polypeptide, protein or protein fragment and the metal ion-affinity peptide, and if the bound recombinant polypeptide, protein or protein fragment is treated with the appropriate enzyme, the target polypeptide, protein or protein fragment may be selectively released while the metal ion-affinity polypeptide fragment remains bound to the immobilized metal. For this purpose, the cleavage is preferably an enzymatically cleavable linker peptide having the ability to undergo site-specific proteolysis. Suitable cleaving enzymes in accordance with this invention are activated factor X (factor Xa), DPP I, DPP II, DPP IV, carboxylpeptidase A, collagen, enterokinase, human renin, thrombin, trypsin, subtilisin and V5.

It is to be appreciated that some polypeptide or protein molecules will possess the desired enzymatic or biological activity with the metal chelate peptide still attached either at the C-terminal end or at the N-terminal end or both. In those cases the purification of the chimeric protein will be accomplished without subjecting the protein to site-specific proteolysis.

The present invention may be used to purify any prokaryotic or eukaryotic protein that can be expressed as the product of recombinant DNA technology in a transformed host cell. These recombinant protein products include hormones, receptors, enzymes, storage proteins, blood proteins, mutant proteins produced by protein engineering techniques, or synthetic proteins. The purification process of the present invention can be used batchwise or in continuously run columns.

It is to be understood that the present invention has been described in detail by way of illustration and example in order to acquaint others skilled in the art with the invention, its principles, and its practical application. Further, the specific embodiments of the present invention as set forth are not intended to be exhaustive or to limit the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but put them forth only as possible explanations in light of current understanding.

ABBREVIATIONS AND DEFINITIONS

To facilitate understanding of the invention, a number of terms are defined below. Definitions of certain terms are included here. Any term not defined is understood to have the normal meaning used by scientists contemporaneous with the submission of this application.

The term "expression vector" as used herein refers to nucleic acid sequences containing a desired coding sequence and appropriate nucleic acid sequences necessary for the expression of the operably linked coding sequence in a particular host organism. Nucleic acid sequences necessary for expression in prokaryotes include a promoter, a ribosome binding site, an initiation codon, a stop codon, optionally an operator sequence and possibly other regulatory sequences. Eukaryotic cells utilize promoters, a Kozak sequence and often enhancers and polyadenlyation signals. Prokaryotic cells also utilize a Shine-Dalgarno Ribosome binding site. The present invention includes vectors or plasmids which can be used as vehicles to transform any viable host cell with the recombinant DNA expression vector.

"Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers, and other expression control elements (e.g., polyadenylation signals). Regulatory sequences include those that direct constitutive expression of a nucleotide sequence in many types of host cell and those that direct expression of the nucleotide sequence only in certain host cells (e.g., tissue-specific regulatory sequences).

The terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in laboratory manuals.

The term "hydrophilic" when used in reference to amino acids refers to those amino acids which have polar and/or charged side chains. Hydrophilic amino acids include lysine, arginine, histidine, aspartate (i.e., aspartic acid), glutamate (i.e., glutamic acid), serine, threonine, cysteine, tyrosine, asparagine and glutamine.

The term "hydrophobic" when used in reference to amino acids refers to those amino acids which have nonpolar side chains. Hydrophobic amino acids include valine, leucine, isoleucine, cysteine and methionine. Three hydrophobic amino acids have aromatic side chains. Accordingly, the term "aromatic" when used in reference to amino acids refers to the three aromatic hydrophobic amino acids phenylalanine, tyrosine and tryptophan.

The term "fusion protein" refers to polypeptides and proteins which comprise a metal ion-affinity linker peptide and a protein or polypeptide operably linked directly or indirectly to the metal ion-affinity peptide. The metal ion-affinity linker peptide may be located at the amino-terminal portion of the fusion protein or at the carboxy-terminal protein thus forming an "amino-terminal fusion protein" or a "carboxy-terminal fusion protein," respectively.

The terms "metal ion-affinity peptide", "metal binding peptide" and "linker peptide" are used interchangeably to refer to an amino acid sequence which displays an affinity to metal ions. The minimum length of the immobilized metal ion-affinity peptide according to the present invention is seven amino acids including four alternating histidines. The most preferred length is seven amino acids including four alternating histidines.

The term "enzyme" referred to herein in the context of a cleavage enzyme means a polypeptide or protein which recognizes a specific amino acid sequence in a polypeptide and cleaves the polypeptide at the scissile bond. In one embodiment of the present invention, enterokinase is the enzyme which is used to free the fusion protein from the immobilized metal ion column. In further embodiments, carboxylpeptidase A, DPP I, DPP II, DPP IV, factor Xa, human renin, TEV, thrombin or VIII protease is the enzyme.

The terms "cleavage site" used herein refers to an amino acid sequence which is recognized and cleaved by an enzyme or chemical means at the scissile bond.

The term "scissile bond" referred to herein is the juncture where cleavage occurs; for example the scissile bond recognized by enterokinase may be the bond following the sequence ($Asp_4$)-Lys in the spacer peptide or affinity peptide.

By the term "immobilized metal ion-affinity peptide" as used herein is meant an amino acid sequence that chelates immobilized divalent metal ions of metals selected from the group consisting of aluminum, cadmium, calcium, cobalt, copper, gallium, iron, nickel, ytterbium and zinc.

The term "capture ligand" means any ligand or receptor that can be immobilized or supported on a container or support and used to isolate a cellular component from cellular debris. Some non-limiting examples of capture ligands that may be used in connection with the present invention include: biotin, streptavidin, various metal chelate ions, antibodies, various charged particles such as those for use in ion exchange chromatography, various affinity chromatography supports, and various hydrophobic groups for use in hydrophobic chromatography.

For all the nucleotide and amino acid sequences disclosed herein, it is understood that equivalent nucleotides and amino acids can be substituted into the sequences without affecting the function of the sequences. Such substitutions is within the ability of a person of ordinary skill in the art.

The procedures disclosed herein which involve the molecular manipulation of nucleic acids are known to those skilled in the art.

EXAMPLES

Example 1

Construction and Screening of a Metal Ion-Affinity Peptide Library

A pseudo-random glutathione-S-transferase C-terminal peptide library was constructed with the amino acid sequence of His-X-His-X-His-X-His where X is any amino acid except Gln, His and Pro. The library vector was constructed from the bacterial expression vector pGEX-2T. The library was constructed by annealing a pair of complimentary oligonucleotides together. Oligonucleotides were constructed as follows: 5'GATCCCATDNDCATDNDCATDNDCATTAAC3' (SEQ ID NO: 18) and 5'AATTGTTAATGHNHATGH-NHATGHNHATGG3' (SEQ ID NO: 19) where D may be a nucleotide selected from the group consisting of nucleotides A, G, and T, H may be a nucleotide selected from the group consisting of nucleotides A, C, and T and N is a nucleotide selected from the group consisting of nucleotides A, C, T, and G. The 5' end was phosphorylated with $T_4$ polynucleotide kinase and the oligonucleotides were annealed together to generate a cassette. The cassette was ligated into pGEX-2T, which had been digested with EcoRI and BamHI restriction endonucleases. Ligated vector was transformed into E. coli DH5-α using standard protocols. Transformants were plated on LB/ampicillin plates (100 mg/L) and incubated overnight at 37° C.

900 colonies were picked and placed on 9 master plates. Each master plate contained 100 colonies each and were grown overnight at 37° C. A piece of nitrocellulose was placed onto each of the master plates. This piece of nitrocellulose was then removed and the transferred colonies were placed onto a LB/ampicillin plate containing 1 mM isopropyl β-D-thiogalactopyranoside (IPTG) to induce the expression of the GST fusion peptides. The cells were allowed to grow for an additional 4 hours at 37° C. The nitrocellulose filter was removed from the plate and placed sequentially on blotting paper containing the following solutions to lyse the cells in situ:

(a) 10% SDS for 10 minutes,
(b) 1.5 M sodium chloride, 0.5 M sodium hydroxide for 5 minutes
(c) 1.5 M sodium chloride, 0.5 M Tris-HCl pH 7.4 for 5 minutes
(d) 1.5 M sodium chloride, 0.5 M Tris-HCl pH 7.4 for 5 minutes
(e) 2×SSC for 15 minutes.

The filters were dried at ambient temperature followed by an incubation in Tris-buffered saline (TBS) containing 3% non-fat dry milk for 1 hour at room temperature. Filters were then washed 3 times for 5 minutes with TBS containing 0.05% Tween-20 (TBS-T). To detect clones that were capable of binding to a metal ion, the filters were incubated with nickel NTA horseradish peroxidase (HRP) at a concentration of 1 mg/ml in TBS-T for 1 hour. The filters were then washed with TBS-T 3 times for 5 minutes and incubated with 3-3'-5-5'-Tetramethylbenzidine (TMB) to detect the horseradish peroxidase. The reaction was stopped by placing the filters in water. 250 colonies, which were detected above, were picked from the master plate and placed into 1 ml of LB/ampicillin and grown overnight in a 96 deep well plate at 37° C. at 250 rpm on an orbital shaker. 10 μl of the overnight cultures were transferred to a fresh aliquot of LB/ampicillin (1 ml) in a 96 deep well plate and grown for an additional 3 hours. The culture was then induced by adding IPTG (final concentration of 1 mM) and the culture was allowed to grow for an additional 3 hours prior to harvesting by centrifugation. The media was decanted and the cells were frozen overnight at −20° C. in the collection plate. Cells were lysed with 0.6 ml of CelLytic-B (Sigma-Aldrich Co., St. Louis, Mo., Product No. B3553) and incubated for 15 minutes at room temperature. The cell debris was removed by centrifugation at 3,000×g for 15 minutes. Two experiments were performed in parallel, one on a His-Select High Sensitivity (HS) nickel coated plate, and the second on HIS-Select High Capacity (HC) nickel coated plate. 0.1 ml of cell extracts of each clone were placed in a HS microwell plate in the presence of imidazole at a final concentration of 5 mM. This is the selective condition used for screening the different metal ion-affinity clones. HS plates were incubated for 4 hours at room temperature. Plates were then washed 3 times with phosphate-buffered saline (PBS) containing 0.05% Tween 20 (PBS-T). The HS plates were then incubated with anti-GST at 1:1,000 dilution in PBS-BSA buffer (0.2 ml/well) for 1 hour at room temperature. HS plates were washed 3 times with PBS-T. The HS plates were then incubated with anti-mouse HRP conjugate at 1:10,000 dilution in PBS-BSA buffer for 1 hour at room temperature. Plates were washed 3× with PBS-T. The plate was then developed with 2,2'azino-bis(3-ethylbenzthiazoline-6-sulfonic acid) ABST substrate. Color development was stopped by the addition of sodium azide to a final concentration of 2 mM. Absorbance of the plates was read at 405 nm using a Wallace 1420 plate reader. The HC plates were used to further analyze potential clones. To further characterize the clones, 0.2 ml of cell extracts were applied to the HC plates and the plates were incubated at ambient temperature for 1 hour. The plates were washed with PBS as described above. Twenty-one clones that produced the highest response on the HS plates were eluted from the corresponding HC plate. The selected cloned proteins were eluted from the HC plates by incubating at 37° C. for 15 minutes in 50 mM sodium phosphate, 0.3 M sodium chloride and 0.2 M imidazole buffer. Eluted proteins were then moved to clean tubes and analyzed by SDS-PAGE. All 21 clones had the expected molecular weight and were sequence verified.

These 21 colonies were grown overnight in 1 ml LB/ampicillin media at 37° C. at 250 rpm. 100 μl of the overnight cultures were transferred to 50 ml of fresh LB/ampicillin media and the cultures grown for an additional 3 hours at 37° C. The cultures were induced with IPTG (final concentration of 1 mM) and the cultures grown for an additional 3 hours prior to harvesting by centrifugation.

Example 2

Construction of an N-Terminal Metal Ion-Affinity Fusion Protein

Two metal ion-affinity tags were introduced to the N-terminal of bacterial alkaline phosphatase (BAP). The constructs were constructed from the BAP expression vector pFLAG-CTS-BAP. Construction was done by annealing two pair of complimentary oligonucleotides together. The following oligonucleotides were constructed: 5'TATGCATAAT-CATCGACATGAACATA3' (SEQ ID NO: 20), 5'AGCTTAT-GTTTATGTCGATGATTATGCA3' (SEQ ID NO: 21), 5'TATGCATAAACATAGACATGGGCATA3' (SEQ ID NO: 22) and 5'AGCTTGATGCCCATGTCTATGTTTATGCA3' (SEQ ID NO: 23). The oligonucleotides were annealed together to generate a cassette. The cassette was ligated into pFLAG-CTS-BAP, which had been digested with NdeI and HindIII restriction endonucleases. Ligated vector was transformed into E. coli DH5-a using standard protocols and plated on LB/ampicillin.

Example 3

Expression of an N-Terminal Metal Ion-Affinity Fusion Protein

MAT-BAP fusion peptide cultures were grown overnight in 1 ml LB/ampicillin at 37° C. 500 μl of overnight cultures were transferred to 500 μl of fresh TB media containing ampicillin (100 mg/L). The cultures were grown for three hours at 37° C. at 250 rpm. Protein expression was induced by the addition of IPTG (final concentration of 1 mM). Cultures were then grown for an additional three hours, harvested by centrifugation and stored at −70° C. until further use.

Example 4

Metal Ion-Affinity Fusion Protein Purification Protocol #1

Cells were resuspended in 2 ml of TE (50 mM Tris-HCl pH 8.0, 2 mM EDTA). Lysozyme (4 mg/ml in 2 ml of TE) was added to the resuspended cells and the cells were lysed at ambient temperature for 4 hours. The cell debris was removed by centrifugation at 27,000×g for 15 minutes. The supernatant was dialyzed overnight against 50 mM Tris-HCl pH 8.0 to remove the EDTA. The dialyzed supernatant was applied to a 1 ml column containing a nickel bis-carboxy-methyl-cysteine resin (nickel resin). The column was washed with 4 ml of 50 mM Tris-HCl pH 8.0 and then washed with 2 ml of 50 mM Tris-HCl pH 8.0, 10 mM imidazole. The column was then eluted 50 mM Tris-HCl pH 8.0 250 mM imidazole. Samples were analyzed for purity by SDS-PAGE.

Example 5

Metal Ion-Affinity Fusion Protein Purification Protocol #2

Cells were resuspended with CelLytic B (Sigma-Aldrich Co., St. Louis, Mo., Product No. B3553), and 10 mM imidazole. The cells were solubilized by incubation for 15 minutes. The cell debris was removed by centrifugation at 15,000×g for 5 minutes at room temperature. A 0.5 ml column, containing nickel resin, was equilibrated with 10 column volumes (5 ml) of 50 mM sodium phosphate, pH 8, and 300 mM sodium chloride (column buffer). The supernatant was loaded on the column. The column was washed with 10 column volumes (5 ml) of 10 mM imidazole in column buffer. The column was eluted with 100 mM imidazole in column buffer. The samples were analyzed for specificity by SDS-PAGE.

Example 6

Metal Ion-Affinity Fusion Protein Purification Protocol #3

Use of Chaotropic Agents

The cells were resuspended in 100 mM sodium phosphate, pH 8, and 8 M urea (denaturant column buffer). The cells were solubilized by sonication three times, 15 seconds each, with a probe sonicator. Cell debris was removed by centrifugation at 15,000×g for 5 minutes at room temperature. A 0.5 ml column, containing nickel resin, was equilibrated with 10 column volumes (5 ml) of the denaturant column buffer. The supernatant was loaded on the column and the column was washed with 10 column volumes (5 ml) of denaturant column buffer. The column was sequentially eluted with 100 mM sodium phosphate, 8 M urea at pH 7.5, 7.0, 6.5, 6.0, 5.5, 5.0 and 4.5. The samples were analyzed for specificity by SDS-PAGE.

Example 7

Producing a Monoclonal Antibody to a MAT Tag Amino Acid Sequence

Mouse monoclonal antibodies were made by standard methods from mice immunized with MAT tag sequence specific peptides.

BALB/c mice were immunized by standard methods with a synthetic MAT tag sequence (HNHRHKH; MAT1) containing peptide (HNHRHKHGGGC (SEQ ID NO: 35) or CGGGHNHRHKH (SEQ ID NO: 36)) conjugated to keyhole limpet hemocyanin (KLH) carrier protein by the C- or N-terminal cysteine. Splenocytes from the immunized mice were fused with mouse melanoma cells (NS1) to form hybridomas, which were screened (by ELISA and/or Western blot immunostaining assays) for reactivity to a C-terminally MAT-tagged glutathione-S-transferase (GST-MAT1) fusion protein versus GST alone. One positive hybridoma clone (MAT 1-87) was selected and propagated. The MAT 1-87 clone was used to generate mouse ascites fluid, from which an anti-MAT monoclonal antibody was purified by Protein A affinity chromatography. Subsequently, the purified anti-MAT antibody from clone MAT 1-87 was shown to be an IgG2a immunoglobulin with specific reactivity to the MAT tag sequence at either the N- or C-terminus of MAT-tagged fusion proteins by Western blot immunostaining.

Example 8

Producing a Polyclonal Antibody to a MAT Tag Amino Acid Sequence

Rabbit polyclonal antibodies were made by standard methods from rabbits immunized with MAT tag sequence specific peptides.

White New Zealand rabbits were immunized by standard methods with a synthetic MAT tag sequence containing peptide (CGGGHNHRHKH (SEQ ID NO: 36) or HNHRH-KHGGGC (SEQ ID NO: 35)) conjugated to KLH by the N- or C-terminal cysteine. The immunized rabbits were bled and the IgG was purified from the serum by peptide antigen affinity purification. The affinity purified antibody to the CGGGHNHRHKH (SEQ ID NO: 36) peptide was shown to react specifically with the MAT tag sequence at the C-terminus of MAT-tagged fusion proteins by Western blot immunostaining.

Example 9

Use of an Anti-MAT Antibody to Detect MAT-Tagged Fusion Protein Expression by Colony Lift Immunostaining Colonies of *Eschericia coli* transformants containing MAT-tagged fusion protein expression plasmids were induced and lysed on nitrocellulose filters. The filters were subsequently immunostained with a monoclonal anti-MAT tag antibody to reveal expression of MAT-tagged fusion proteins.

Open reading frames of ten different *E. coli* proteins were cloned into an expression vector in frame with a C-terminal MAT tag. Each construct was transformed into competent cells of an *E. coli* expression strain (strain BL21). Transformant colonies were selected for ampicillin (50 µg/ml) resistance on Luria-Bertani medium (LB) agar growth plates. Transformant colonies were lifted with nitrocellulose filter circles onto plates containing 0.1 M isopropyl-β-D-thiogalatoside (IPTG) and induced for four hours at 37° C. The induced colonies were lysed on the nitrocellulose filters by setting each filter colony side up on a 1 ml drop of Western transfer buffer (48 mM Tris, 39 mM glycine, 0.375% sodium dodecyl sulfate, 20% methanol, pH 9.2) for 30 minutes at room temperature. The filters were blocked with 1% bovine serum albumin (BSA) in phosphate buffered saline (PBS) (Sigma-Aldrich Co., St. Louis, Mo., Product No. P3688) and were immunostained by standard methods using anti-MAT monoclonal antibody (clone MAT 1-87; 0.5 µg/ml), followed by rabbit anti-mouse IgG-horse radish peroxidase (HRP) conjugate (1/1000 dilution; Sigma-Aldrich Co., St. Louis, Mo., Product No. A9044). The antibody dilutions were made in blocking buffer. The filters were developed and visualized with 3,3',5,5' Tetramethylbenzidine (TMB) liquid substrate (Sigma-Aldrich Co., St. Louis, Mo., Product No. T0565).

The anti-MAT monoclonal antibody readily detected differential expression of MAT-tagged fusion proteins from the induced *E. coli* transformants on the immunostained colony lift filters.

Example 10

Use of an Anti-MAT Antibody to Detect MAT-Tagged Fusion Protein by Western Blot Immunostaining Colonies of *Eschericia coli* transformants containing MAT-tagged fusion protein expression plasmids were grown and induced in liquid culture. The induced cells were harvested, lysed and analyzed for fusion protein expression by Western blot immunostaining. The Western blots were immunostained with a monoclonal anti-MAT tag antibody to reveal expression of MAT-tagged fusion proteins.

Transformant colonies of the ten MAT-tagged fusion protein constructs described in Example 9 were grown in liquid culture (LB) with ampicillin selection (50 µg/ml) to mid-log phase ($A_{600}$=0.8) and subsequently induced with 0.1 M IPTG for four hours at 37° C. The induced cells were harvested by centrifugation and lysed by boiling for five minutes in Laemmli sample buffer (Sigma-Aldrich Co., St. Louis, Mo., Product No. S3401). Samples of the lysates were separated by SDS-PAGE, followed by Western blotting. The Western blot was blocked with 1% bovine serum albumin (BSA) in phosphate buffered saline (PBS) (Sigma-Aldrich Co., St. Louis, Mo., Product No. P3688) and were immunostained by standard methods using anti-MAT monoclonal antibody (clone MAT 1-87; 0.5 µg/ml), followed by rabbit anti-mouse IgG-HRP conjugate (1/1000 dilution; Sigma-Aldrich Co., St. Louis, Mo., Product No. A9044). The antibody dilutions were in blocking solution. The immunostained blot was developed and visualized with 3,3',5,5' Tetramethylbenzidine (TMB) liquid substrate (Sigma-Aldrich Co., St. Louis, Mo., Product No. T0565).

The anti-MAT monoclonal antibody readily detected the expressed MAT-tagged fusion proteins, and fragments thereof, from the induced *E. coli* transformants on the Western blot. No background, non-specific reactivity with the endogenous *E. coli* proteins in the lysates was detected.

Example 11

Use of an Anti-MAT Antibody to Detect MAT-Tagged Fusion Protein Expression by Immunostaining Cells Mammalian cells were grown and transiently transfected with a MAT-tagged fusion protein expression construct. The transfected cells were immunostained with a monoclonal anti-MAT tag antibody to reveal expression of the MAT-tagged fusion protein.

Adherent 293T cells were grown on microscope slide cover slips in tissue culture dishes and transfected with a FLAG-MAT-MAP Kinase expression vector. After two days expression, the cells were fixed and permeabilized with 3% paraformaldehyde and 0.5% Triton X-100. The permeabilized cells were stained with 5 µg/ml anti-MAT monoclonal antibody (clone MAT 1-87) and developed with anti-mouse IgG (Fab specific)-FITC conjugate (Sigma-Aldrich Co., St. Louis, Mo., Product No. F5262) at a 1/40 dilution.

Staining of transfected cells expressing the MAT-tagged fusion protein could be seen in the cytoplasm and nuclei of the cells by fluorescence microscopy. There was no staining of transfected cells that were immunostained without the anti-MAT monoclonal antibody. Also, non-expressing transfected cells and control mock transfected cells did not stain with the anti-MAT antibody.

Example 12

Use of an Anti-MAT Antibody for Capture of MAT-Tagged Fusion Protein by Immunoprecipitation (Affinity Purification)

We tested the ability of an anti-MAT monoclonal antibody to capture specifically a MAT-tagged fusion protein from a complex biochemical mixture. A purified MAT-tagged fusion protein was spiked into a mammalian cell lysate and was efficiently captured by immunoprecipitation (IP) with an anti-MAT monoclonal antibody.

A 27 kDa target fusion protein (GST) with a C-terminal MAT tag was expressed in *E. coli* and purified by immobilized metal affinity chromatography (IMAC). The purified 27 kDa MAT-tagged fusion protein was spiked into a COS-7 cell lysate ($10^7$ cells in 1 ml Radio-Immunoprecipitation Assay buffer; RIPA buffer, Sigma-Aldrich Co., St. Louis, Mo., Product No. R0278) at 25 µg/ml. The target protein was affinity captured from the lysate by immunoprecipitation using an anti-MAT monoclonal antibody (clone MAT 1-87; 50 µg/ml) and EZview® Red Protein G Affinity Gel (Sigma-Aldrich Co., St. Louis, Mo., Product No. F3403). After washing the affinity gel samples, the bound proteins were eluted by boiling in Laemmli sample buffer and analyzed by SDS-PAGE with Coomassie staining (EZBlue® Gel Staining Reagent, Sigma-Aldrich Co., St. Louis, Mo., Product No. G1041).

A stained band of the captured and eluted MAT-tagged target protein could be seen easily on the stained gel, migrating at the 27 kDa region of the gel, slightly above the light chain of the anti-MAT IgG (25 kDa). The MAT-tagged protein was captured by the anti-MAT monoclonal antibody efficiently and specifically. No contaminating, non-specific proteins were detected in a parallel IP of the lysate without the spiked MAT-tagged target protein.

Example 13

Comparison of Monoclonal Anti-MAT Antibody to Monoclonal Anti-Polyhistidine Antibody in Western Blot Immunostaining Monoclonal antibodies to a polyhistidine (6×His) tag and to the MAT tag were compared for performance for detecting their respective tagged target proteins by immunostaining Western blots. The anti-MAT monoclonal antibody gave less background with stronger specific signal on the immunostained blot.

A 27 kDa target fusion protein (GST) with a C-terminal polyhistidine (6×His) tag and the same 27 kDa target fusion protein with a C-terminal MAT tag each was expressed in *E. coli* by standard methods as in Example 10. Lysates from uninduced and four hour induced cells for each construct were separated by SDS-PAGE and analyzed by Western blot immunostaining. The blot was blocked with 3% non-fat dry milk in Tris-buffered saline (TBS). The portion of the blot containing the polyhistidine-tagged target protein samples was immunostained with anti-polyhistidine antibody (Sigma-Aldrich Co., St. Louis, Mo., Product No. H1029) diluted to 0.5 µg/ml in blocking solution. The portion of the blot containing the MAT-tagged protein samples was immunostained using anti-MAT monoclonal antibody (clone MAT 1-87) diluted to 0.5 µg/ml in blocking solution. Subsequently, both portions of the blot were washed in Tris-buffered saline (TBS; Sigma-Aldrich Co., St. Louis, Mo., Product No. T6664) and incubated with rabbit anti-mouse IgG-HRP conjugate (Sigma-Aldrich Co., St. Louis, Mo., Product No. A9044) diluted 1/1000 in blocking solution. Then both portions of the immunostained blot were washed thoroughly with TBS containing 0.05% Tween 20 and were developed and visualized with 3,3',5,5' Tetramethylbenzidine (TMB) liquid substrate (Sigma-Aldrich Co., St. Louis, Mo., Product No. T0565).

The anti-MAT monoclonal antibody gave a stronger staining signal for the MAT-tagged target protein with less non-specific background staining on the blot than the anti-polyhistidine monoclonal antibody staining for the 6×His-tagged target protein, which showed a weaker specific signal with stronger non-specific background staining. The anti-MAT monoclonal antibody displayed a clear advantage in this Western blot immunostaining system.

Example 14

Use of an Anti-MAT Antibody to Evaluate Expressed MAT-Tagged Fusion Protein Translation Products in a Dual-Tag System Fusion Protein by Western Blot Immunostaining A target protein construct was made with a FLAG tag at the N-terminus and a MAT tag at the C-terminus. Induced cells carrying the dual-tagged construct were harvested, lysed and analyzed for fusion protein expression by Western blot immunostaining with both an anti-FLAG and an anti-MAT antibody. Only the full-length fusion protein was stained by both antibodies.

The coding region for bacterial alkaline phosphatase (BAP) was cloned into an *E. coli* expression vector with an N-terminal FLAG tag and a C-terminal MAT tag. Transformed *E. coli* cells containing this construct were grown in liquid culture (LB) with ampicillin selection (50 µg/ml) to mid-log phase ($A_{600}$=0.8) and subsequently induced with 0.1 M IPTG for four hours at 37° C. The induced cells were harvested by centrifugation and lysed by boiling for five minutes in Laemmli sample buffer (Sigma-Aldrich Co., St. Louis, Mo., Product No. S3401). Duplicate samples of the lysates were separated by SDS-PAGE, followed by Western blotting. The Western blots were blocked with 1% bovine serum albumin (BSA) in phosphate buffered saline (PBS) (Sigma-Aldrich Co., St. Louis, Mo., Product No. P3688) and were immunostained by standard methods. The Western blot containing one set of the duplicate samples was immunostained using Anti-FLAG-HRP conjugate (Sigma-Aldrich Co., St. Louis, Mo., Product No. A8592; 1/1000 dilution). The other set was immunostained using an anti-MAT monoclonal antibody (clone MAT 1-87; 0.5 µg/ml), followed by rabbit anti-mouse IgG-HRP conjugate (Sigma-Aldrich Co., St. Louis, Mo., Product No. A9044). Both immunostained blots were developed and visualized with 3,3',5,5' Tetramethylbenzidine (TMB) liquid substrate (Sigma-Aldrich Co., St. Louis, Mo., Product No. T0565).

The anti-FLAG and the anti-MAT antibodies each specifically recognized the full-length fusion protein containing both the N- and C-terminal tags. In addition, each antibody recognized different subsets of smaller fusion protein fragments containing only either the N- or C-terminal tag, indicating that most of the smaller fragments were derived from full-length fusion protein, which had been endoproteolytically cleaved.

What is claimed is:

1. An antibody that binds to a metal ion-affinity peptide in a polypeptide, protein or protein fragment represented by the formula $R_1$-$Sp_1$-(His-$Z_1$-His-Arg-His-$Z_2$-His)-$Sp_2$-$R_2$, wherein (His-$Z_1$-His-Arg-His-$Z_2$-His) is the metal ion-affinity peptide, $R_1$ is hydrogen, a polypeptide, protein or protein fragment; $Sp_1$ is a covalent bond or a spacer comprising at least one amino acid residue; $R_2$ is hydrogen, a polypeptide, protein or protein fragment; $Sp_2$ is a covalent bond or a spacer comprising at least one amino acid residue; $Z_1$ is an amino acid residue selected from the group consisting of Ala, Arg, Asn, Asp, Gln, Glu, Ile, Lys, Phe, Pro, Ser, Thr, Trp, and Val; and $Z_2$ is an amino acid residue selected from the group consisting of Ala, Arg, Asn, Asp, Cys, Gln, Glu, Gly, Ile, Leu, Lys, Met, Pro, Ser, Thr, Tyr, and Val.

2. The antibody of claim 1, wherein $Z_1$ and $Z_2$ are selected from the following combinations:
   (a) $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr and Tyr;
   (b) $Z_1$ is selected from the group consisting of Asn and Lys, $Z_2$ is selected from the group consisting of Gly and Lys;
   (c) $Z_1$ is Ile and $Z_2$ is Asn;
   (d) $Z_1$ is Thr and $Z_2$ is Ser;
   (e) $Z_1$ is Ser and $Z_2$ is Tyr;
   (f) $Z_1$ is Val and $Z_2$ is Ala;
   (g) $Z_1$ is Ala and $Z_2$ is Lys;
   (h) $Z_1$ is Asn and $Z_2$ is Lys; and
   (l) $Z_1$ is Lys and $Z_2$ is Gly.

3. The antibody of claim 1, wherein $R_1$ or $R_2$ are independently selected from hydrogen or an amino acid residue.

4. The antibody of claim 1, wherein $Sp_1$ or $Sp_2$ is a spacer comprising a proteolytic cleavage site, a fusion protein, a secretion sequence, a leader sequence for cellular targeting, an epitope or an internal ribosomal sequences.

5. The antibody of claim 1, wherein $Sp_1$ or $Sp_2$ is a spacer comprising a proteolytic cleavage site.

6. The antibody of claim 5, wherein the proteolytic cleavage site is cleaved with enterokinase.

7. The antibody of claim 1, wherein at least one of $Sp_1$, $Sp_2$, $R_1$ and $R_2$ comprises at least one of the amino acid sequences selected from the group consisting of SEQ ID NOS: 1-17.

8. The antibody of claim 1, wherein $Sp_1$ or $Sp_2$ is a spacer comprising the enzyme glutathione-S-transferase of the parasite helminth *Schistosoma japonicum*.

9. The antibody of claim 1, wherein $Sp_1$ or $Sp_2$ is a spacer comprising the amino acid sequence DYKDDDDK (SEQ ID NO:15).

10. The antibody of claim 1, wherein $Sp_1$ or $Sp_2$ is a spacer comprising the amino acid sequence DLYDDDDK (SEQ ID NO:16).

11. The antibody of claim 1, wherein $Sp_1$ or $Sp_2$ is a spacer comprising the amino acid sequence Met-Asp-Tyr-Lys-Asp-His-Asp-Gly-Asp-Tyr-Lys-Asp-His-Asp-Ile-Asp-Tyr-Lys-Asp-Asp-Asp-Asp-Lys (SEQ ID NO:17).

12. The antibody of claim 1, wherein $Sp_1$ or $Sp_2$ is a spacer comprising a polypeptide possessing an amino acid having at least 70% homology to any one of the amino acid sequences disclosed in SEQ ID NOS: 1-17 and having the same binding characteristics as said amino acid.

13. The antibody of claim 1, wherein the antibody is purified.

14. An antibody that binds to a metal ion-affinity peptide in a polypeptide, protein or protein fragment represented by the formula $R_1$-$Sp_1$-(His-$Z_1$-His-Arg-His-$Z_2$-His)$_t$-$Sp_2$-$R_2$, wherein (His-$Z_1$-His-Arg-His-$Z_2$-His) is the metal ion-affinity peptide, t is at least 2, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue, $Z_1$ is an amino acid residue selected from the group consisting of Ala, Arg, Asn, Asp, Gln, Glu, Ile, Lys, Phe, Pro, Ser, Thr, Trp, and Val, and Z2 is an amino acid residue selected from the group consisting of Ala, Arg, Asn, Asp, Cys, Gln, Glu, Gly, Ile, Leu, Lys, Met, Pro, Ser, Thr, Tyr, and Val.

15. The antibody of claim 14, wherein $Z_1$ and $Z_2$ are selected from the following combinations:
   (a) $Z_1$ is Asn and $Z_2$ is Lys; and
   (b) $Z_1$ is Lys and $Z_2$ is Gly.

16. The antibody of claim 14, wherein the antibody is purified.

17. An antibody that binds to a metal ion-affinity peptide in a polypeptide, protein or protein fragment represented by the formula $R_1$-$Sp_1$-[(His-$Z_1$-His-Arg-His-$Z_2$-His)-$Sp_2$]$_t$-$R_2$, wherein (His-$Z_1$-His-Arg-His-$Z_2$-His) is the metal ion-affinity peptide, t is at least 2, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue, $Z_1$ is an amino acid residue selected from the group consisting of Ala, Arg, Asn, Asp, Gln, Glu, Ile, Lys, Phe, Pro, Ser, Thr, Trp, and Val, and $Z_2$ is an amino acid residue selected from the group consisting of Ala, Arg, Asn, Asp, Cys, Gln, Glu, Gly, Ile, Leu, Lys, Met, Pro, Ser, Thr, Tyr, and Val; and each $Sp_2$ of the recombinant polypeptides, proteins or protein fragments may be the same or different.

18. The antibody of claim 17, wherein $Z_1$ and $Z_2$ are selected from the following combinations:
   (a) $Z_1$ is Asn and $Z_2$ is Lys; and
   (b) $Z_1$ is Lys and $Z_2$ is Gly.

19. The antibody of claim 17, wherein the antibody is purified.

20. A process for detecting, identifying, isolating, capturing or purifying a polypeptide, protein, or protein fragment in or from a sample, the process comprising combining an antibody of claim 1 with the sample to bind the polypeptide, protein or protein fragment to the antibody.

21. The process of claim 20, wherein the antibody is immobilized.

22. The process of claim 20, wherein the antibody is labeled.

23. The process of claim 20, further comprising releasing the polypeptide, protein, protein fragment, or a portion thereof from the antibody.

24. The process of claim 20, wherein the process additionally comprises combining the polypeptide, protein, protein fragment, or a portion thereof with an immobilized metal ion.

25. The process of claim 24, wherein the polypeptide, protein, protein fragment, or a portion thereof is combined with an immobilized metal ion before being combined with an antibody of claim 1.

26. The process of claim 24, wherein the polypeptide, protein, protein fragment, or a portion thereof is combined with an immobilized metal ion after being combined with an antibody of claim 1.

27. The process of claim 20, wherein the polypeptide, protein, or protein fragment comprises a first tag, a second tag, and a polypeptide, protein, or protein fragment positioned in between the first and second tag, wherein either the first or the second tag is a metal ion-affinity peptide, and the other tag is selected from the group consisting of the amino acid sequence DYKDDDDK (SEQ ID NO:15), the amino acid sequence DLYDDDDK (SEQ ID NO:16), the amino acid sequence DYKDHDGDYKDHDIDYKDDDDK (SEQ ID NO:41), the amino acid sequence DLYDHDGDLYDH-DIDLYDDDDK (SEQ ID NO:42), GST, HA, c-myc, and GFP.

28. The process of claim 27, wherein the first tag and the second tag are selected from the following combinations:

(a) the first tag is DYKDDDDK (SEQ ID NO:15) and the second tag is a metal ion-affinity peptide;
(b) the first tag is DLYDDDDK (SEQ ID NO:16) and the second tag is a metal ion-affinity peptide;
(c) the first tag is DYKDHDGDYKDHDIDYKDDDDK (SEQ ID NO:41) and the second tag is a metal ion-affinity peptide;
(d) the first tag is DLYDHDGDLYDHDIDLYDDDDK (SEQ ID NO:42) and the second tag is a metal ion-affinity peptide;
(e) the first tag is GST and the second tag is a metal ion-affinity peptide;
(f) the first tag is GFP and the second tag is a metal ion-affinity peptide;
(g) the first tag is HA and the second tag is a metal ion-affinity peptide; and
(h) the first tag is c-myc and the second tag is a metal ion-affinity peptide.

29. The process of claim 27, wherein the first tag and the second tag are selected from the following combinations:

(a) the first tag is a metal ion-affinity peptide and the second tag is DYKDDDDK (SEQ ID NO:15);
(b) the first tag is a metal ion-affinity peptide and the second tag is DLYDDDDK (SEQ ID NO:16);
(c) the first tag is a metal ion-affinity peptide and the second tag is DYKDHDGDYKDHDIDYKDDDDK (SEQ ID NO:41);
(d) the first tag is a metal ion-affinity peptide and the second tag is DLYDHDGDLYDHDIDLYDDDDK (SEQ ID NO:42);
(e) the first tag is a metal ion-affinity peptide and the second tag is GST;
(f) the first tag is a metal ion-affinity peptide and the second tag is GFP
(g) the first tag is a metal ion-affinity peptide and the second tag is HA; and
(h) the first tag is a metal ion-affinity peptide and the second tag is c-myc.

\* \* \* \* \*

UNITED STATES PATENT AND TRADEMARK OFFICE
CERTIFICATE OF CORRECTION

| | | |
|---|---|---|
| PATENT NO. | : 7,741,053 B2 | Page 1 of 1 |
| APPLICATION NO. | : 11/128486 | |
| DATED | : June 22, 2010 | |
| INVENTOR(S) | : Richard J. Mehigh et al. | |

It is certified that error appears in the above-identified patent and that said Letters Patent is hereby corrected as shown below:

Col. 79, line 6: "Gin" should be --Gln--

Col. 79, line 27: "sequences" should be --sequence--

Col. 79, line 67: "Z2" should be --$Z_2$--

Col. 82, line 14: "GFP" should be --GFP;--

Signed and Sealed this
First Day of February, 2011

David J. Kappos
*Director of the United States Patent and Trademark Office*